US012049608B2

(12) United States Patent
Miracle et al.

(10) Patent No.: US 12,049,608 B2
(45) Date of Patent: *Jul. 30, 2024

(54) LEUCO COLORANTS AS BLUING AGENTS IN LAUNDRY CARE COMPOSITIONS

(71) Applicant: The Procter & Gamble Company, Cincinnati, OH (US)

(72) Inventors: Gregory Scot Miracle, Liberty Township, OH (US); Daniel Dale Ditullio, Hamilton, OH (US); Dominick Joseph Valenti, Moore, SC (US); Sanjeev Kumar Dey, Spartanburg, SC (US); Haihu Qin, Greer, SC (US)

(73) Assignee: The Procter & Gamble Company, Cincinnati, OH (US)

( * ) Notice: Subject to any disclaimer, the term of this patent is extended or adjusted under 35 U.S.C. 154(b) by 301 days.

This patent is subject to a terminal disclaimer.

(21) Appl. No.: 15/800,111

(22) Filed: Nov. 1, 2017

(65) Prior Publication Data

US 2018/0119065 A1 May 3, 2018

Related U.S. Application Data

(60) Provisional application No. 62/415,575, filed on Nov. 1, 2016.

(51) Int. Cl.
| | | |
|---|---|---|
| *C11D 3/42* | (2006.01) | |
| *A61N 1/05* | (2006.01) | |
| *A61N 1/36* | (2006.01) | |
| *A61N 1/372* | (2006.01) | |
| *A61N 1/375* | (2006.01) | |
| *C09B 11/00* | (2006.01) | |
| *C09B 11/04* | (2006.01) | |
| *C09B 11/10* | (2006.01) | |
| *C09B 11/12* | (2006.01) | |
| *C09B 57/00* | (2006.01) | |
| *C11D 3/00* | (2006.01) | |
| *C11D 3/18* | (2006.01) | |
| *C11D 3/20* | (2006.01) | |
| *C11D 3/26* | (2006.01) | |

(52) U.S. Cl.
CPC .............. *C11D 3/42* (2013.01); *A61N 1/0541* (2013.01); *A61N 1/36038* (2017.08); *A61N 1/36139* (2013.01); *A61N 1/372* (2013.01); *A61N 1/3752* (2013.01); *C09B 11/12* (2013.01); *C09B 57/00* (2013.01); *C11D 3/0084* (2013.01); *C11D 3/187* (2013.01); *C11D 3/20* (2013.01); *C11D 3/26* (2013.01)

(58) Field of Classification Search
CPC .......... C11D 3/42; C09B 11/00; C09B 11/04; C09B 11/10
See application file for complete search history.

(56) References Cited

U.S. PATENT DOCUMENTS

| | | |
|---|---|---|
| 5,800,500 A | 9/1998 | Spelman et al. |
| 7,544,216 B2 | 6/2009 | Torres |
| 7,597,723 B2 | 10/2009 | Moore |
| 7,637,963 B2 | 12/2009 | Moore |
| 8,293,695 B2 | 10/2012 | Hohener |
| 9,206,382 B2 | 12/2015 | Lant |
| 9,982,221 B2 * | 5/2018 | Qin ..................... C09B 11/10 |
| 10,723,982 B2 * | 7/2020 | Qin ..................... C09B 11/12 |
| 10,851,329 B2 * | 12/2020 | Valenti ................ C08G 75/00 |
| 11,053,392 B2 * | 7/2021 | Qin ..................... C11D 3/40 |
| 2008/0234793 A1 | 9/2008 | Gibson |
| 2015/0246234 A1 | 9/2015 | Hazard et al. |
| 2015/0322384 A1 * | 11/2015 | Butterfield ........... C09B 11/10 510/324 |
| 2016/0137956 A1 | 5/2016 | Hayward |
| 2016/0312158 A1 | 10/2016 | Miracle |
| 2016/0326467 A1 * | 11/2016 | Qin ..................... C09B 11/06 |
| 2018/0119057 A1 | 5/2018 | Ditullio |
| 2018/0119058 A1 | 5/2018 | Miracle |
| 2018/0119059 A1 | 5/2018 | Miracle |
| 2018/0119060 A1 | 5/2018 | Miracle |
| 2018/0119061 A1 | 5/2018 | Miracle |
| 2018/0119062 A1 | 5/2018 | Miracle |
| 2018/0119063 A1 | 5/2018 | Miracle |
| 2018/0119064 A1 | 5/2018 | Miracle |
| 2018/0119065 A1 | 5/2018 | Miracle |
| 2018/0119066 A1 | 5/2018 | Miracle |
| 2018/0119067 A1 | 5/2018 | Miracle |
| 2018/0119068 A1 | 5/2018 | Miracle |
| 2018/0119069 A1 | 5/2018 | Miracle |
| 2018/0119070 A1 | 5/2018 | Miracle |
| 2018/0155656 A1 | 6/2018 | Miracle et al. |

FOREIGN PATENT DOCUMENTS

| | | | |
|---|---|---|---|
| CN | 101600765 B | 7/2014 | |
| EP | 355864 * | 2/1990 | ............. C09B 11/12 |
| EP | 2573144 B1 | 6/2016 | |
| IN | 268918 B | 9/2015 | |
| WO | WO 2008/100445 * | 8/2008 | ............... C11D 3/42 |
| WO | WO2008100445 A2 | 8/2008 | |
| WO | WO2016178668 A1 | 11/2016 | |
| WO | 2019075150 A1 | 4/2019 | |

OTHER PUBLICATIONS

International Search Report; International Application No. PCT/US2017/059423; dated Jan. 24, 2018; 12 pages.

* cited by examiner

*Primary Examiner* — Brian P Mruk
(74) *Attorney, Agent, or Firm* — George H. Leal; Carolyn S. Powell

(57) ABSTRACT

A laundry care composition including: (a) at least one laundry care ingredient and (b) a leuco composition. The laundry care composition has a ΔHA of at least 10. Methods of treating textiles with such laundry care compositions.

7 Claims, No Drawings

LEUCO COLORANTS AS BLUING AGENTS IN LAUNDRY CARE COMPOSITIONS

TECHNICAL FIELD

This application describes laundry care compositions that contain leuco colorants and their use in the laundering of textile articles. These types of colorants are provided in a stable, substantially colorless state and then may be transformed to an intense colored state upon exposure to certain physical or chemical changes such as, for example, exposure to oxygen, ion addition, exposure to light, and the like. The laundry care compositions containing the leuco colorants are designed to enhance the apparent or visually perceived whiteness of, or to impart a desired hue to, textile articles washed or otherwise treated with the laundry care composition.

JOINT RESEARCH AGREEMENT

The inventions described and claimed herein were made pursuant to a Joint Research Agreement between The Procter & Gamble Company and Milliken & Company (Spartanburg, S.C., USA).

BACKGROUND

As textile substrates age, their color tends to fade or yellow due to exposure to light, air, soil, and natural degradation of the fibers that comprise the substrates. As such, to visually enhance these textile substrates and counteract the fading and yellowing the use of polymeric colorants for coloring consumer products has become well known in the prior art. For example, it is well known to use whitening agents, either optical brighteners or bluing agents, in textile applications. However, due to the blue or violet hue of traditional bluing agents, formulators have been constrained to using traditional bluing agents in blue laundry care compositions or, otherwise concealing the bluing agent as a blue speckle in a granule compositions or including it in the blue compartment of a unit dose.

Leuco dyes are also known in the prior art to exhibit a change from a colorless or slightly colored state to a colored state upon exposure to specific chemical or physical triggers. The change in coloration that occurs is typically visually perceptible to the human eye. All existing compounds have some absorbance in the visible light region (400-750 nm), and thus more or less have some color. In this invention, a dye is considered as a "leuco dye" if it did not render a significant color at its application concentration and conditions, but renders a significant color in its triggered form. The color change upon triggering stems from the change of the molar attenuation coefficient (also known as molar extinction coefficient, molar absorption coefficient, and/or molar absorptivity in some literatures) of the leuco dye molecule in the 400-750 nm range, preferably in the 500-650 nm range, and most preferably in the 530-620 nm range. The increase of the molar attenuation coefficient of a leuco dye before and after the triggering should be bigger than 50%, more preferably bigger than 200%, and most preferably bigger than 500%.

As such, there remains a need for a bluing agent that delivers the desired consumer whiteness benefit but also gives formulation flexibility to the color and design of the laundry care composition.

It has now surprisingly been found that the presently claimed leuco colorants not only provide the desired consumer whiteness benefit, but provide flexibility to select various laundry care composition colors and forms, and in some embodiments, have a Transparency Rating of 1 or higher, as described further in the Method Section herein.

SUMMARY OF THE INVENTION

In one aspect, the present invention provides a laundry care composition comprising: (a) at least one laundry care ingredient and (b) a leuco composition. The laundry care composition has a $\Delta HA$ of at least 10.

The present invention further encompasses methods for treating textile articles with a laundry care composition according to the present invention.

DETAILED DESCRIPTION

Definitions

As used herein, the term "alkoxy" is intended to include $C_1$-$C_8$ alkoxy and alkoxy derivatives of polyols having repeating units such as butylene oxide, glycidol oxide, ethylene oxide or propylene oxide.

As used herein, the interchangeable terms "alkyleneoxy" and "oxyalkylene," and the interchangeable terms "polyalkyleneoxy" and "polyoxyalkylene," generally refer to molecular structures containing one or more than one, respectively, of the following repeating units: —$C_2H_4O$—, —$C_3H_6O$—, —$C_4H_8O$—, and any combinations thereof. Non-limiting structures corresponding to these groups include —$CH_2CH_2O$—, —$CH_2CH_2CH_2O$—, —$CH_2CH_2CH_2CH_2O$—, —$CH_2CH(CH_3)O$—, and —$CH_2CH(CH_2CH_3)O$—, for example. Furthermore, the polyoxyalkylene constituent may be selected from the group consisting of one or more monomers selected from a $C_{2\text{-}20}$ alkyleneoxy group, a glycidyl group, or mixtures thereof.

The terms "ethylene oxide," "propylene oxide" and "butylene oxide" may be shown herein by their typical designation of "EO," "PO" and "BO," respectively.

As used herein, the terms "alkyl" and "alkyl capped" are intended to mean any univalent group formed by removing a hydrogen atom from a substituted or unsubstituted hydrocarbon. Non-limiting examples include hydrocarbyl moieties which are branched or unbranched, substituted or unsubstituted including $C_1$-$C_{18}$ alkyl groups, and in one aspect, $C_1$-$C_6$ alkyl groups.

As used herein, unless otherwise specified, the term "aryl" is intended to include $C_3$-$C_{12}$ aryl groups. The term "aryl" refers to both carbocyclic and heterocyclic aryl groups.

As used herein, the term "alkaryl" refers to any alkyl-substituted aryl substituents and aryl-substituted alkyl substituents. More specifically, the term is intended to refer to $C_7$-$C_{16}$ alkyl-substituted aryl substituents and $C_7$-$C_{16}$ aryl substituted alkyl substituents which may or may not comprise additional substituents.

As used herein, the term "detergent composition" is a sub-set of laundry care composition and includes cleaning compositions including but not limited to products for laundering fabrics. Such compositions may be pre-treatment composition for use prior to a washing step or may be rinse added compositions, as well as cleaning auxiliaries, such as bleach additives and "stain-stick" or pre-treat types.

As used herein, the term "laundry care composition" includes, unless otherwise indicated, granular, powder, liquid, gel, paste, unit dose, bar form and/or flake type washing agents and/or fabric treatment compositions, including but not limited to products for laundering fabrics, fabric softening compositions, fabric enhancing compositions, fabric freshening compositions, and other products for the care and maintenance of fabrics, and combinations thereof. Such compositions may be pre-treatment compositions for use prior to a washing step or may be rinse added compositions, as well as cleaning auxiliaries, such as bleach additives and/or "stain-stick" or pre-treat compositions or substrate-laden products such as dryer added sheets.

As used herein, the term "leuco" (as used in reference to, for example, a compound, moiety, radical, dye, monomer, fragment, or polymer) refers to an entity (e.g., organic compound or portion thereof) that, upon exposure to specific chemical or physical triggers, undergoes one or more chemical and/or physical changes that results in a shift from a first color state (e.g., uncolored or substantially colorless) to a second more highly colored state. Suitable chemical or physical triggers include, but are not limited to, oxidation, pH change, temperature change, and changes in electromagnetic radiation (e.g., light) exposure. Suitable chemical or physical changes that occur in the leuco entity include, but are not limited to, oxidation and non-oxidative changes, such as intramolecular cyclization. Thus, in one aspect, a suitable leuco entity can be a reversibly reduced form of a chromophore. In one aspect, the leuco moiety preferably comprises at least a first and a second π-system capable of being converted into a third combined conjugated π-system incorporating said first and second π-systems upon exposure to one or more of the chemical and/or physical triggers described above.

As used herein, the terms "leuco composition" or "leuco colorant composition" refers to a composition comprising at least two leuco compounds having independently selected structures as described in further detail herein.

As used herein "average molecular weight" of the leuco colorant is reported as a weight average molecular weight, as determined by its molecular weight distribution: as a consequence of their manufacturing process, the leuco colorants disclosed herein may contain a distribution of repeating units in their polymeric moiety.

As used herein, the terms "maximum extinction coefficient" and "maximum molar extinction coefficient" are intended to describe the molar extinction coefficient at the wavelength of maximum absorption (also referred to herein as the maximum wavelength), in the range of 400 nanometers to 750 nanometers.

As used herein, the term "first color" is used to refer to the color of the laundry care composition before triggering, and is intended to include any color, including colorless and substantially colorless.

As used herein, the term "second color" is used to refer to the color of the laundry care composition after triggering, and is intended to include any color that is distinguishable, either through visual inspection or the use of analytical techniques such as spectrophotometric analysis, from the first color of the laundry care composition.

As used herein, the term "converting agent" refers to any oxidizing agent as known in the art other than molecular oxygen in any of its known forms (singlet and triplet states).

As used herein, the term "triggering agent" refers to a reactant suitable for converting the leuco composition from a colorless or substantially colorless state to a colored state.

As used herein, the term "whitening agent" refers to a dye or a leuco colorant that may form a dye once triggered that when on white cotton provides a hue to the cloth with a relative hue angle of 210 to 345, or even a relative hue angle of 240 to 320, or even a relative hue angle of 250 to 300 (e.g., 250 to 290).

As used herein, "cellulosic substrates" are intended to include any substrate which comprises at least a majority by weight of cellulose. Cellulose may be found in wood, cotton, linen, jute, and hemp. Cellulosic substrates may be in the form of powders, fibers, pulp and articles formed from powders, fibers and pulp. Cellulosic fibers, include, without limitation, cotton, rayon (regenerated cellulose), acetate (cellulose acetate), triacetate (cellulose triacetate), and mixtures thereof. Articles formed from cellulosic fibers include textile articles such as fabrics. Articles formed from pulp include paper.

As used herein, articles such as "a" and "an" when used in a claim, are understood to mean one or more of what is claimed or described.

As used herein, the terms "include/s" and "including" are meant to be non-limiting.

As used herein, the term "solid" includes granular, powder, bar and tablet product forms.

As used herein, the term "fluid" includes liquid, gel, paste and gas product forms.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

In one aspect, the molar extinction coefficient of said second colored state at the maximum absorbance in the wavelength in the range 200 to 1,000 nm (more preferably 400 to 750 nm) is preferably at least five times, more preferably 10 times, even more preferably 25 times, most preferably at least 50 times the molar extinction coefficient of said first color state at the wavelength of the maximum absorbance of the second colored state. Preferably, the molar extinction coefficient of said second colored state at the maximum absorbance in the wavelength in the range 200 to 1,000 nm (more preferably 400 to 750 nm) is at least five times, preferably 10 times, even more preferably 25 times, most preferably at least 50 times the maximum molar extinction coefficient of said first color state in the corresponding wavelength range. An ordinarily skilled artisan will realize that these ratios may be much higher. For example, the first color state may have a maximum molar extinction coefficient in the wavelength range from 400 to 750 nm of as little as 10 $M^{-1}cm^{-1}$, and the second colored state may have a maximum molar extinction coefficient in the wavelength range from 400 to 750 nm of as much as 80,000 $M^{-1}cm^{-1}$ or more, in which case the ratio of the extinction coefficients would be 8,000:1 or more.

In one aspect, the maximum molar extinction coefficient of said first color state at a wavelength in the range 400 to 750 nm is less than 1000 $M^{-1}cm^{-1}$, and the maximum molar extinction coefficient of said second colored state at a wavelength in the range 400 to 750 nm is more than 5,000 $M^{-1}cm^{-1}$, preferably more than 10,000, 25,000, 50,000 or even 100,000 $M^{-1}cm^{-1}$.

A skilled artisan will recognize and appreciate that a polymer comprising more than one leuco moiety may have a significantly higher maximum molar extinction coefficient in the first color state (e.g., due to the additive effect of a multiplicity of leuco moieties or the presence of one or more leuco moieties converted to the second colored state). Where more than one leuco moiety is attached to a molecule, the maximum molar extinction coefficient of said second color state may be more than n×ε where n is the number of leuco moieties plus oxidized leuco moieties present on the molecule, and ε is selected from 5,000 $M^{-1}cm^{-1}$, preferably more than 10,000, 25,000, 50,000 or even 100,000 $M^{-1}cm^{-1}$. Thus, for a molecule that has two leuco moieties, the maximum molar extinction coefficient of said second color state may be more than 10,000 $M^{-1}cm^{-1}$, preferably more than 20,000, 50,000, 100,000 or even 200,000 $M^{-1}cm^{-1}$. While n could theoretically be any integer, one skilled in the art appreciates that n will typically be from 1 to 100, more preferably 1 to 50, 1 to 25, 1 to 10 or even 1 to 5.

The amount of leuco colorant used in the laundry care compositions of the present invention may be any level suitable to achieve the aims of the invention. In one aspect, the laundry care composition comprises leuco colorant in an amount from about 0.0001 wt % to about 1.0 wt %, preferably from 0.0005 wt % to about 0.5 wt %, even more preferably from about 0.0008 wt % to about 0.2 wt %, most preferably from 0.004 wt % to about 0.1 wt %.

In another aspect, the laundry care composition comprises leuco colorant in an amount from 0.0025 to 5.0 milliequivalents/kg, preferably from 0.005 to 2.5 milliequivalents/kg, even more preferably from 0.01 to 1.0 milliequivalents/kg, most preferably from 0.05 to 0.50 milliequivalents/kg, wherein the units of milliequivalents/kg refer to the milliequivalents of leuco moiety per kg of the laundry composition. For leuco colorants comprising more than one leuco moiety, the number of milliequivalents is related to the number of millimoles of the leuco colorant by the following equation: (millimoles of leuco colorant)×(no. of milliequivalents of leuco moiety/millimole of leuco colorant)=milliequivalents of leuco moiety. In instances where there is only a single leuco moiety per leuco colorant, the number of milliequivalents/kg will be equal to the number of millimoles of leuco colorant/kg of the laundry care composition.

The present invention relates to a class of leuco colorants that may be useful for use in laundry care compositions, such as liquid laundry detergent, to provide a hue to whiten textile substrates. Leuco colorants are compounds that are essentially colorless or only lightly colored but are capable of developing an intense color upon activation. One advantage of using leuco compounds in laundry care compositions is that such compounds, being colorless until activated, allow the laundry care composition to exhibit its own color. The leuco colorant generally does not alter the primary color of the laundry care composition. Thus, manufacturers of such compositions can formulate a color that is most attractive to consumers without concern for added ingredients, such as bluing agents, affecting the final color value of the composition.

The range of textile articles encountered in the consumer home is quite large and often comprises garments constructed from a wide variety of both natural and synthetic fibers, as well as mixtures of these either in the same wash load or even in the same garment. The articles can be constructed in a variety of ways and may comprise any of a vast array of finishes that may be applied by the manufacturer. The amount of any such finish remaining on a consumer's textile article depends on a wide array of factors among which are the durability of the finish under the particular washing conditions employed by the consumer, the particular detergents and additives the consumer may have used as well as the number of cycles that the article has been washed. Depending on the history of each article, finishes may be present to varying degrees or essentially absent, while other materials present in the wash or rinse cycles and contaminants encountered during wearing may start to accumulate on the article.

The skilled artisan is keenly aware that any detergent formulation used by consumers will encounter textile articles that represent the full range of possibilities and expects that there not only may be, but in fact will be, significant differences in the way the formulation performs on some textiles articles as opposed to others. These differences can be found through routine experimentation. For example, the leuco colorants of the present invention have been found in some instances to increase the whiteness of consumer aged garments and also garments to which fabric enhancers have been applied, more than they increase the whiteness of new garments from which the finishes have been removed with successive washes. Thus, formulations comprising such leuco colorants may be preferred over traditional formulations, even formulations containing conventional hueing agents, since newer garments typically have less of a yellowing issue whereas older consumer aged garments are more prone to have an issue with yellowing. These leuco colorants have a bias for increasing the whiteness of aged garments over clean new garments that is larger than the bias displayed by many traditional hueing agents.

In one aspect, the invention relates to a leuco composition selected from the group consisting of a diarylmethane leuco, a triarylmethane leuco, an oxazine leuco, a thiazine leuco, a hydroquinone leuco, an arylaminophenol leuco and mixtures thereof.

Suitable diarylmethane leuco compounds for use herein include, but are not limited to, diarylmethylene derivatives capable of forming a second colored state as described herein. Suitable examples include, but are not limited to, Michler's methane, a diarylmethylene substituted with an —OH group (e.g., Michler's hydrol) and ethers and esters thereof, a diarylmethylene substituted with a photocleavable moiety, such as a —CN group (bis(para-N,N-dimethyl)phenyl)acetonitrile), and similar such compounds.

In one aspect, the invention relates to a composition comprising one or more leuco compounds conforming to the group selected from:

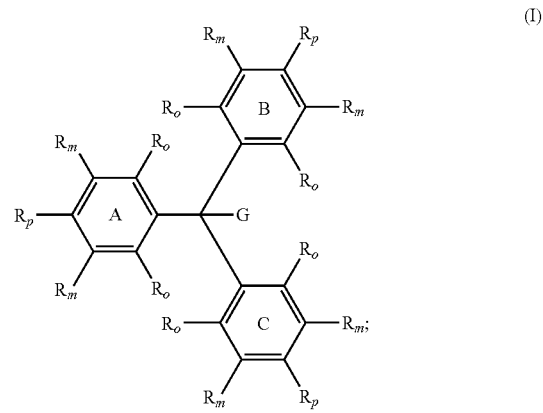

(I)

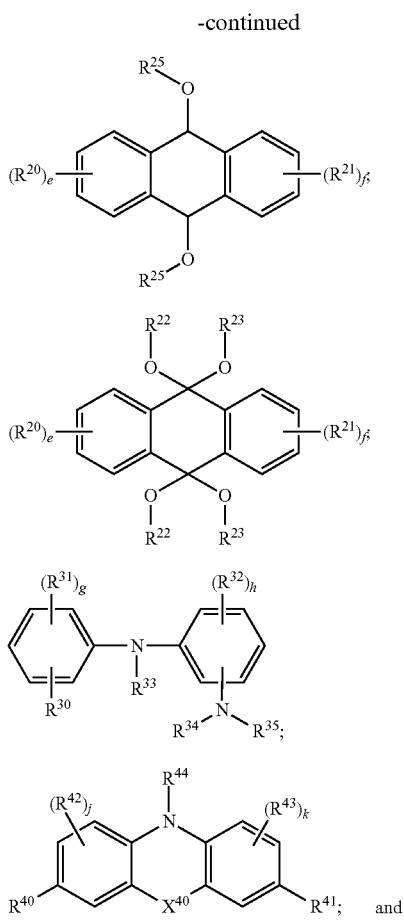

(f) mixtures thereof;
wherein the ratio of Formula I-V to its oxidized form is at least 1:19, 1:9, or 1:3, preferably at least 1:1, more preferably at least 3:1, most preferably at least 9:1 or even 19:1.

In the structure of Formula (I), wherein each individual $R_o$, $R_m$ and $R_p$ group on each of rings A, B and C is independently selected from the group consisting of hydrogen, deuterium and $R^5$; each $R^5$ is independently selected from the group consisting of halogens, nitro, alkyl, substituted alkyl, aryl, substituted aryl, alkaryl, substituted alkaryl, —$(CH_2)_n$—O—$R^1$, —$(CH_2)_n NR^1R^2$, —$C(O)R^1$, —$C(O)OR^1$, —$C(O)O^-$, —$C(O)NR^1R^2$, —$OC(O)R^1$, —$OC(O)OR^1$, —$OC(O)NR^1R^2$, —$S(O)_2R^1$, —$S(O)_2OR^1$, —$S(O)_2O^-$, —$S(O)_2NR^1R^2$, —$NR^1C(O)R^2$, —$NR^1C(O)OR^2$, —$NR^1C(O)SR^2$, —$NR^1C(O)NR^2R^3$, —$P(O)_2R^1$, —$P(O)(OR^1)_2$, —$P(O)(OR^1)O^-$, and —$P(O)(O^-)_2$, wherein the index n is an integer from 0 to 4, preferably from 0 to 1, most preferably 0; wherein two $R_o$ on different A, B and C rings may combine to form a fused ring of five or more members; when the fused ring is six or more members, two $R_o$ on different A, B and C rings may combine to form an organic linker optionally containing one or more heteroatoms; in one embodiment two $R_o$ on different A, B and C rings combine to form a heteroatom bridge selected from —O— and —S— creating a six member fused ring; an $R_o$ and $R_m$ on the same ring or an $R_m$ and $R_p$ on the same ring may combine to form a fused aliphatic ring or fused aromatic ring either of which may contain heteroatoms; on at least one of the three rings A, B or C, preferably at least two, more preferably at least three, most preferably all four of the $R_o$ and $R_m$ groups are hydrogen, preferably all four $R_o$ and $R_m$ groups on at least two of the rings A, B and C are hydrogen; in some embodiments, all $R_o$ and $R_m$ groups on rings A, B and C are hydrogen; preferably each $R_p$ is independently selected from hydrogen, —$OR^1$ and —$NR^1R^2$; no more than two, preferably no more than one of $R_p$ is hydrogen, preferably none are hydrogen; more preferably at least one, preferably two, most preferably all three $R_p$ are —$NR^1R^2$; in some embodiments, one or even two of the Rings A, B and C may be replaced with an independently selected $C_3$-$C_9$ heteroaryl ring comprising one or two heteroatoms independently selected from O, S and N, optionally substituted with one or more independently selected $R^5$ groups; G is independently selected from the group consisting of hydrogen, deuterium, $C_1$-$C_{16}$ alkoxide, phenoxide, bisphenoxide, nitrite, nitrile, alkyl amine, imidazole, arylamine, polyalkylene oxide, halides, alkylsulfide, aryl sulfide, or phosphine oxide; in one aspect the fraction [(deuterium)/(deuterium+hydrogen)] for G is at least 0.20, preferably at least 0.40, even more preferably at least 0.50 and most preferably at least 0.60 or even at least 0.80; wherein any two of $R^1$, $R^2$ and $R^3$ attached to the same heteroatom can combine to form a ring of five or more members optionally comprising one or more additional heteroatoms selected from the group consisting of —O—, —$NR^{15}$—, and —S—.

In the structure of Formula (II)-(III), e and f are independently integers from 0 to 4; each $R^{20}$ and $R^{21}$ is independently selected from the group consisting of halogens, a nitro group, alkyl groups, substituted alkyl groups, —NC(O)OR$^1$, —NC(O)SR$^1$, —OR$^1$, and —NR$^1R^2$; each $R^{25}$ is independently selected from the group consisting of monosaccharide moiety, disaccharide moiety, oligosaccharide moiety, and polysaccharide moiety, —$C(O)R^1$, —$C(O)OR^1$, —$C(O)NR^1R^2$; each $R^{22}$ and $R^{23}$ is independently selected from the group consisting of hydrogen, alkyl groups, and substituted alkyl groups.

In the structure of Formula (IV), $R^{30}$ is positioned ortho or para to the bridging amine moiety and is selected from the group consisting of —$OR^{38}$ and —$NR^{36}R^{37}$, each $R^{36}$ and $R^{37}$ is independently selected from the group consisting of hydrogen, alkyl groups, substituted alkyl groups, aryl groups, substituted aryl groups, acyl groups, $R^4$, —$C(O)OR^1$, —$C(O)R^1$, and —$C(O)NR^1R^2$; $R^{38}$ is selected from the group consisting of hydrogen, acyl groups, —$C(O)OR^1$, —$C(O)R^1$, and —$C(O)NR^1R^2$; g and h are independently integers from 0 to 4; each $R^{31}$ and $R^{32}$ is independently selected from the group consisting of alkyl groups, substituted alkyl groups, aryl groups, substituted aryl groups, alkaryl, substituted alkaryl, —$(CH_2)_n$—O—$R^1$, —$(CH_2)_n$—$NR^1R^2$, —$C(O)R^1$, —$C(O)OR^1$, —$C(O)O^-$, —$C(O)NR^1R^2$, —$OC(O)R^1$, —$OC(O)OR^1$, —$OC(O)NR^1R^2$, —$S(O)_2R^1$, —$S(O)_2OR^1$, —$S(O)_2O^-$, —$S(O)_2NR^1R^2$, —$NR^1C(O)R^2$, —$NR^1C(O)OR^2$, —$NR^1C(O)SR^2$, —$NR^1C(O)NR^2R^3$, —$P(O)_2R^1$, —$P(O)(OR^1)_2$, —$P(O)(OR^1)O^-$, and —$P(O)(O^-)_2$, wherein the index n is an integer from 0 to 4, preferably from 0 to 1, most preferably 0; —$NR^{34}R^{35}$ is positioned ortho or para to the bridging amine moiety and $R^{34}$ and $R^{35}$ are independently selected from the group consisting of hydrogen, alkyl, substituted alkyl, aryl, substituted aryl, alkaryl, substituted alkaryl, and $R^4$; $R^{33}$ is independently selected from the group consisting of hydrogen, —$S(O)_2R^1$, —$C(O)N(H)R^1$; —$C(O)OR^1$; and —$C(O)R^1$; when g is 2 to 4, any two adjacent $R^{31}$ groups may combine to form a fused ring of five or more members wherein no more than two of the atoms in the fused ring may be nitrogen atoms;

In the structure of Formula (V), $X^{40}$ is selected from the group consisting of an oxygen atom, a sulfur atom, and $NR^{45}$; $R^{45}$ is independently selected from the group consisting of hydrogen, deuterium, alkyl, substituted alkyl, aryl, substituted aryl, alkaryl, substituted alkaryl, —S(O)$_2$OH, —S(O)$_2$O$^-$, —C(O)OR$^1$, —C(O)R$^1$, and —C(O)NR$^1$R$^2$; $R^{40}$ and $R^{41}$ are independently selected from the group consisting of —(CH$_2$)$_n$—O—R$^1$, —(CH$_2$)$_n$—NR$^1$R$^2$, wherein the index n is an integer from 0 to 4, preferably from 0 to 1, most preferably 0; j and k are independently integers from 0 to 3; $R^{42}$ and $R^{43}$ are independently selected from the group consisting of alkyl, substituted alkyl, aryl, substituted aryl, alkaryl, substituted alkaryl, —S(O)$_2$R$^1$, —C(O)NR$^1$R$^2$, —NC(O)OR$^1$, —NC(O)SR$^1$, —C(O)OR$^1$, —C(O)R$^1$, —(CH$_2$)$_n$—O—R$^1$, —(CH$_2$)$_n$—NR$^1$R$^2$, wherein the index n is an integer from 0 to 4, preferably from 0 to 1, most preferably 0; $R^{44}$ is —C(O)R$^1$, —C(O)NR$^1$R$^2$, and —C(O)OR$^1$;

In the structures of Formula (I)-(V), wherein any charge present in any of the preceeding groups is balanced with a suitable independently selected internal or external counterion. Suitable independently selected external counterions may be cationic or anionic. Examples of suitable cations include but are not limited to one or more metals preferably selected from Group I and Group II, the most preferred of these being Na, K, Mg, and Ca, or an organic cation such as iminium, ammonium, and phosphonium. Examples of suitable anions include but are not limited to: fluoride, chloride, bromide, iodide, perchlorate, hydrogen sulfate, sulfate, aminosulfate, nitrate, dihydrogen phosphate, hydrogen phosphate, phosphate, bicarbonate, carbonate, methosulfate, ethosulfate, cyanate, thiocyanate, tetrachlorozincate, borate, tetrafluoroborate, acetate, chloroacetate, cyanoacetate, hydroxyacetate, aminoacetate, methylaminoacetate, di- and tri-chloroacetate, 2-chloro-propionate, 2-hydroxypropionate, glycolate, thioglycolate, thioacetate, phenoxyacetate, trimethylacetate, valerate, palmitate, acrylate, oxalate, malonate, crotonate, succinate, citrate, methylene-bis-thioglycolate, ethylene-bis-iminoacetate, nitrilotriacetate, fumarate, maleate, benzoate, methylbenzoate, chlorobenzoate, dichlorobenzoate, hydroxybenzoate, aminobenzoate, phthalate, terephthalate, indolylacetate, chlorobenzenesulfonate, benzenesulfonate, toluenesulfonate, biphenylsulfonate and chlorotoluenesulfonate. Those of ordinary skill in the art are well aware of different counterions which can be used in place of those listed above.

In the structures of Formula (I)-(V), $R^1$, $R^2$, $R^3$, and $R^{15}$ are independently selected from the group consisting of hydrogen, alkyl, substituted alkyl, aryl, substituted aryl, alkaryl, substituted alkaryl, and $R^4$; wherein $R^4$ is a organic group composed of one or more organic monomers with said monomer molecular weights ranging from 28 to 500, preferably 43 to 350, even more preferably 43 to 250, wherein the organic group may be substituted with one or more additional leuco colorant moieties conforming to the structure of Formula I-V. In one aspect, $R^4$ is selected from the group consisting of alkyleneoxy (polyether), oxoalkyleneoxy (polyesters), oxoalkyleneamine (polyamides), epichlorohydrin, quaternized epichlorohydrin, alkyleneamine, hydroxyalkylene, acyloxyalkylene, carboxyalkylene, carboalkoxyalkylene, and sugar. Where any leuco colorant comprises an $R^4$ group with three or more contiguous monomers, that leuco colorant is defined herein as a "polymeric leuco colorant". One skilled in the art knows that the properties of a compound with regard to any of a number of characteristic attributes such as solubility, partitioning, deposition, removal, staining, etc., are related to the placement, identity and number of such contiguous monomers incorporated therein. The skilled artisan can therefore adjust the placement, identity and number of such contiguous monomers to alter any particular attribute in a more or less predictable fashion.

The leuco compounds described above are believed to be suitable for use in the treatment of textile materials, such as in domestic laundering processes. In particular, it is believed that the leuco compounds will deposit onto the fibers of the textile material due to the nature of the leuco compound. Further, once deposited onto the textile material, the leuco compound can be converted to a colored compound through the application of the appropriate chemical or physical triggers that will convert the leuco compound to its colored form. For example, the leuco compound can be converted to its colored form upon oxidation of the leuco compound to the oxidized compound. By selecting the proper leuco moiety, the leuco compound can be designed to impart a desired hue to the textile material as the leuco compound is converted to its colored form. For example, a leuco compound that exhibits a blue hue upon conversion to its colored form can be used to counteract the yellowing of the textile material that normally occurs due to the passage of time and/or repeated launderings. Thus, in other embodiments, the invention provides laundry care compositions comprising the above-described leuco compound and domestic methods for treating a textile material (e.g., methods for washing an article of laundry or clothing).

Preferably the leuco compound gives a hue to the cloth with a relative hue angle of 210 to 345, or even a relative hue angle of 240 to 320, or even a relative hue angle of 250 to 300 (e.g., 250 to 290). The relative hue angle can be determined by any suitable method as known in the art. However, preferably it may be determined as described in further detail herein with respect to deposition of the leuco entity on cotton relative to cotton absent any leuco entity.

In one preferred embodiment, the Hue Angle (h*) of the laundry care composition and the Relative Hue Angle (RHA) delivered by the leuco colorant, as determined by the methods disclosed hereinafter, are different. The ΔHA between the h* of the laundry care composition and the RHA of the fabric washed in the laundry care composition, calculated according to:

$$\Delta HA = |(h^* - RHA)|,$$

is at least 5, 10, 15, 20, 25, 30, 40, 50, 60, 70, 80, 90, 105, 120, 140 or 160

In a preferred embodiment, the laundry care composition is transparent with a Transparency Rating of at least 1 or more preferably, a Transparency Rating of 2, 3, 4, 5 or even 6, as determined by the methods disclosed in further detail herein.

Laundry Care Ingredients

The laundry care composition may comprise other suitable adjuncts which, in some aspects, can be wholly or partially incorporated. Adjuncts may be selected according to the laundry care composition's intended function. The first composition may comprise an adjunct. In some aspects, in the case of multi-compartment unit dose articles, the adjuncts may be part of a non-first (e.g., second, third, fourth, etc.) composition encapsulated in compartments separate from the first composition. The non-first composition may be any suitable composition. The non-first composition may be in the form of a solid, a liquid, a dispersion, a gel, a paste or a mixture thereof. Where the unit dose comprises multiple compartments, the leuco colorant may be added to or present in one, two, or even all the compartments. In one embodiment, the leuco colorant is added to the larger compartment, leading to a lower concentration which may minimize any issues involved with potential contact staining. On the other hand, concentrating an anti-oxidant with a leuco colorant in a smaller volume compartment may lead to a higher local concentration of anti-oxidant which may provide enhanced stability. Therefore, as one skilled in the art would appreciate, the formulator can select the location and amount of the leuco colorant according to the desired properties of the unit dose.

Adjuncts

The laundry care composition may comprise a surfactant system. The laundry care composition may comprise from about 1% to about 80%, or from 1% to about 60%, preferably from about 5% to about 50% more preferably from about 8% to about 40%, by weight of the laundry care composition, of a surfactant system Surfactant: Suitable surfactants include anionic surfactants, non-ionic surfactant, cationic surfactants, zwitterionic surfactants and amphoteric surfactants and mixtures thereof. Suitable surfactants may be linear or branched, substituted or un-substituted, and may be derived from petrochemical material or biomaterial. Preferred surfactant systems comprise both anionic and nonionic surfactant, preferably in weight ratios from 90:1 to 1:90. In some instances a weight ratio of anionic to nonionic surfactant of at least 1:1 is preferred. However a ratio below 10:1 may be preferred. When present, the total surfactant level is preferably from 0.1% to 60%, from 1% to 50% or even from 5% to 40% by weight of the subject composition.

Anionic surfactant: Anionic surfactants include, but are not limited to, those surface-active compounds that contain an organic hydrophobic group containing generally 8 to 22 carbon atoms or generally 8 to 18 carbon atoms in their molecular structure and at least one water-solubilizing group preferably selected from sulfonate, sulfate, and carboxylate so as to form a water-soluble compound. Usually, the hydrophobic group will comprise a C8-C 22 alkyl, or acyl group. Such surfactants are employed in the form of water-soluble salts and the salt-forming cation usually is selected from sodium, potassium, ammonium, magnesium and mono-, with the sodium cation being the usual one chosen.

Anionic surfactants of the present invention and adjunct anionic cosurfactants, may exist in an acid form, and said acid form may be neutralized to form a surfactant salt which is desirable for use in the present detergent compositions. Typical agents for neutralization include the metal counterion base such as hydroxides, e.g., NaOH or KOH. Further preferred agents for neutralizing anionic surfactants of the present invention and adjunct anionic surfactants or cosurfactants in their acid forms include ammonia, amines, oligamines, or alkanolamines Alkanolamines are preferred. Suitable non-limiting examples including monoethanolamine, diethanolamine, triethanolamine, and other linear or branched alkanolamines known in the art; for example, highly preferred alkanolamines include 2-amino-1-propanol, 1-aminopropanol, monoisopropanolamine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Suitable sulphonate surfactants include methyl ester sulphonates, alpha olefin sulphonates, alkyl benzene sulphonates, especially alkyl benzene sulphonates, preferably $C_{10-13}$ alkyl benzene sulphonate. Suitable alkyl benzene sulphonate (LAS) is obtainable, preferably obtained, by sulphonating commercially available linear alkyl benzene (LAB). Suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic surfactant is alkyl benzene sulphonate that is obtained by DETAL catalyzed process, although other synthesis routes, such as HF, may also be suitable. In one aspect a magnesium salt of LAS is used.

Suitable sulphate surfactants include alkyl sulphate, preferably $C_{8-18}$ alkyl sulphate, or predominantly $C_{12}$ alkyl sulphate.

A preferred sulphate surfactant is alkyl alkoxylated sulphate, preferably alkyl ethoxylated sulphate, preferably a $C_{8-18}$ alkyl alkoxylated sulphate, preferably a $C_{8-18}$ alkyl ethoxylated sulphate, preferably the alkyl alkoxylated sulphate has an average degree of alkoxylation of from 0.5 to 20, preferably from 0.5 to 10, preferably the alkyl alkoxylated sulphate is a $C_{8-18}$ alkyl ethoxylated sulphate having an average degree of ethoxylation of from 0.5 to 10, preferably from 0.5 to 5, more preferably from 0.5 to 3. The alkyl alkoxylated sulfate may have a broad alkoxy distribnution or a peaked alkoxy distribution.

The alkyl sulphate, alkyl alkoxylated sulphate and alkyl benzene sulphonates may be linear or branched, including 2 alkyl substituted or mid chain branched type, substituted or un-substituted, and may be derived from petrochemical material or biomaterial. Preferably, the branching group is an alkyl. Typically, the alkyl is selected from methyl, ethyl, propyl, butyl, pentyl, cyclic alkyl groups and mixtures thereof. Single or multiple alkyl branches could be present on the main hydrocarbyl chain of the starting alcohol(s) used to produce the sulfated anionic surfactant used in the detergent of the invention. Most preferably the branched sulfated anionic surfactant is selected from alkyl sulfates, alkyl ethoxy sulfates, and mixtures thereof.

Alkyl sulfates and alkyl alkoxy sulfates are commercially available with a variety of chain lengths, ethoxylation and branching degrees. Commercially available sulfates include those based on Neodol alcohols ex the Shell company, Lial—Isalchem and Safol ex the Sasol company, natural alcohols ex The Procter & Gamble Chemicals company.

Other suitable anionic surfactants include alkyl ether carboxylates, comprising a C10-C26 linear or branched, preferably C10-C20 linear, most preferably C16-C18 linear alkyl alcohol and from 2 to 20, preferably 7 to 13, more preferably 8 to 12, most preferably 9.5 to 10.5 ethoxylates. The acid form or salt form, such as sodium or ammonium salt, may be used, and the alkyl chain may contain one cis or trans double bond. Alkyl ether carboxylic acids are available from Kao (Akypo®), Huntsman (Empicol®) and Clariant (Emulsogen®).

Non-ionic surfactant: Suitable non-ionic surfactants are selected from the group consisting of: $C_{8-18}$ alkyl ethoxylates, such as, NEODOL® non-ionic surfactants from Shell; $C_6$-$C_{12}$ alkyl phenol alkoxylates wherein preferably the alkoxylate units are ethyleneoxy units, propyleneoxy units or a mixture thereof; $C_{12}$-$C_{18}$ alcohol and $C_6$-$C_{12}$ alkyl phenol condensates with ethylene oxide/propylene oxide block polymers such as Pluronic® from BASF; alkylpolysaccharides, preferably alkylpolyglycosides; methyl ester ethoxylates; polyhydroxy fatty acid amides; ether capped poly(oxyalkylated) alcohol surfactants; and mixtures thereof.

Suitable non-ionic surfactants are alkylpolyglucoside and/or an alkyl alkoxylated alcohol.

Suitable non-ionic surfactants include alkyl alkoxylated alcohols, preferably $C_{8-18}$ alkyl alkoxylated alcohol, preferably a $C_{8-18}$ alkyl ethoxylated alcohol, preferably the alkyl alkoxylated alcohol has an average degree of alkoxylation of from 1 to 50, preferably from 1 to 30, or from 1 to 20, or from 1 to 10, preferably the alkyl alkoxylated alcohol is a $C_{8-18}$ alkyl ethoxylated alcohol having an average degree of ethoxylation of from 1 to 10, preferably from 1 to 7, more preferably from 1 to 5 and most preferably from 3 to 7. In one aspect, the alkyl alkoxylated alcohol is a $C_{12-15}$ alkyl ethoxylated alcohol having an average degree of ethoxylation of from 7 to 0. The alkyl alkoxylated alcohol can be linear or branched, and substituted or un-substituted. Suitable nonionic surfactants include those with the trade name Lutensol® from BASF.

Cationic surfactant: Suitable cationic surfactants include alkyl pyridinium compounds, alkyl quaternary ammonium compounds, alkyl quaternary phosphonium compounds, alkyl ternary sulphonium compounds, and mixtures thereof.

Preferred cationic surfactants are quaternary ammonium compounds having the general formula:

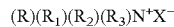

$(R)(R_1)(R_2)(R_3)N^+X^-$ wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, preferred anions include: halides, preferably chloride; sulphate; and sulphonate.

Amphoteric and Zwitterionic surfactant: Suitable amphoteric or zwitterionic surfactants include amine oxides, and/or betaines. Preferred amine oxides are alkyl dimethyl amine oxide or alkyl amido propyl dimethyl amine oxide, more preferably alkyl dimethyl amine oxide and especially coco dimethyl amino oxide. Amine oxide may have a linear or mid-branched alkyl moiety. Typical linear amine oxides include water-soluble amine oxides containing one R1 C8-18 alkyl moiety and 2 R2 and R3 moieties selected from the group consisting of C1-3 alkyl groups and C1-3 hydroxyalkyl groups. Preferably amine oxide is characterized by the formula R1-N(R2)(R3)O wherein R1 is a C8-18 alkyl and R2 and R3 are selected from the group consisting of methyl, ethyl, propyl, isopropyl, 2-hydroxethyl, 2-hydroxypropyl and 3-hydroxypropyl. The linear amine oxide surfactants in particular may include linear C10-C18 alkyl dimethyl amine oxides and linear C8-C12 alkoxy ethyl dihydroxy ethyl amine oxides.

Other suitable surfactants include betaines, such as alkyl betaines, alkylamidobetaine, amidazoliniumbetaine, sulfobetaine (INCI Sultaines) as well as Phosphobetaines.

Leuco Colorant Diluent

Another class of ingredients in the leuco colorants composition may be a diluent and/or solvent. The purpose of the diluent and/or solvent is often, but not limited to, improving fluidity and/or reducing the viscosity of the leuco colorant. Although water is often the preferred diluent and/or solvent given its low cost and non-toxicity, other solvent may also be used as well. The preferred solvent is one having low cost and low hazards. Examples of suitable solvents include, but are not limited to, ethylene glycol, propylene glycol, glycerin, alkoxylated polymers such as polyethylene glycol, polypropylene glycol, copolymers of ethylene oxide and propylene oxide, Tween 20®, Tween 40®, Tween 80®, and the like, and combinations thereof. Among the polymers, the ethylene oxide and propylene oxide copolymers may be preferred. These polymers often feature a cloud point with water, which can help the product separated from the water to remove the undesirable water soluble impurities. Examples of ethylene oxide and propylene oxide copolymers include but not limited to the PLURONIC series polymers by BASF and TERGITOL™ series polymer and by Dow. When the leuco colorant composition is incorporated into the laundry care composition, these polymers may also act as a non-ionic surfactant.

The laundry care compositions described herein may also include one or more of the following non-limiting list of ingredients: fabric care benefit agent; detersive enzyme; deposition aid; rheology modifier; builder; chelant; bleach; bleaching agent; bleach precursor; bleach booster; bleach catalyst; perfume and/or perfume microcapsules; perfume loaded zeolite; starch encapsulated accord; polyglycerol esters; whitening agent; pearlescent agent; enzyme stabilizing systems; scavenging agents including fixing agents for anionic dyes, complexing agents for anionic surfactants, and mixtures thereof; optical brighteners or fluorescers; polymer including but not limited to soil release polymer and/or soil suspension polymer; dispersants; antifoam agents; non-aqueous solvent; fatty acid; suds suppressors, e.g., silicone suds suppressors; cationic starches; scum dispersants; substantive dyes; colorants; opacifier; antioxidant; hydrotropes such as toluenesulfonates, cumenesulfonates and naphthalenesulfonates; color speckles; colored beads, spheres or extrudates; clay softening agents; anti-bacterial agents. Additionally or alternatively, the compositions may comprise surfactants, quaternary ammonium compounds, and/or solvent systems. Quaternary ammonium compounds may be present in fabric enhancer compositions, such as fabric softeners, and comprise quaternary ammonium cations that are positively charged polyatomic ions of the structure $NR_4^+$, where R is an alkyl group or an aryl group Hueing Dye The composition may comprise an additional fabric shading agent. Suitable fabric shading agents include dyes, dye-clay conjugates, and pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof. Preferered dyes include alkoxylated azothiophenes, Solvent Violet 13, Acid Violet 50 and Direct Violet 9.

Aesthetic Colorants. The composition may comprise one or more aesthetic colorants. Suitable aesthetic colorants include dyes, dye-clay conjugates, pigments, and Liquitint® polymeric colorants (Milliken & Company, Spartanburg, S.C., USA). In one aspect, suitable dyes and pigments include small molecule dyes and polymeric dyes. The aesthetic colorant may include at least one chromophore constituent selected from the group consisting of acridines, anthraquinones, azines, azos, benzodifuranes, benzodifuranones, carotenoids, coumarins, cyanines, diazahemicyanines, diphenylmethanes, formazans, hemicyanines, indigoids, methanes, methines, naphthalimides, naphthoquinones, nitros, nitrosos, oxazines, phenothiazine, phthalocyanines (such as copper phthalocyanines), pyrazoles, pyrazolones, quinolones, stilbenes, styryls, triarylmethanes (such as triphenylmethanes), xanthenes, and mixtures thereof.

In one aspect of the invention, aesthetic colorants include Liquitint® Blue AH, Liquitint® Blue BB, Liquitint® Blue 275, Liquitint® Blue 297, Liquitint® Blue BB, Cyan 15, Liquitint® Green 101, Liquitint® Orange 272, Liquitint® Orange 255, Liquitint® Pink AM, Liquitint® Pink AMC, Liquitint® Pink ST, Liquitint® Violet 129, Liquitint® Violet LS, Liquitint® Violet 291, Liquitint® Yellow FT, Liquitint®

Blue Buf, Liquitint® Pink AM, Liquitint® Pink PV, Acid Blue 80, Acid Blue 182, Acid Red 33, Acid Red 52, Acid Violet 48, Acid Violet 126, Acid Blue 9, Acid Blue 1, and mixtures thereof.

Encapsulates. The composition may comprise an encapsulated material. In one aspect, an encapsulate comprising a core, a shell having an inner and outer surface, said shell encapsulating said core. The core may comprise any laundry care adjunct, though typically the core may comprise material selected from the group consisting of perfumes; brighteners; hueing dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polyvinylalcohols, optionally containing other co-monomers; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

Preferred encapsulates comprise perfume. Preferred encapsulates comprise a shell which may comprise melamine formaldehyde and/or cross linked melamine formaldehyde. Other preferred capsules comprise a polyacrylate based shell. Preferred encapsulates comprise a core material and a shell, said shell at least partially surrounding said core material, is disclosed. At least 75%, 85% or even 90% of said encapsulates may have a fracture strength of from 0.2 MPa to 10 MPa, and a benefit agent leakage of from 0% to 20%, or even less than 10% or 5% based on total initial encapsulated benefit agent. Preferred are those in which at least 75%, 85% or even 90% of said encapsulates may have (i) a particle size of from 1 microns to 80 microns, 5 microns to 60 microns, from 10 microns to 50 microns, or even from 15 microns to 40 microns, and/or (ii) at least 75%, 85% or even 90% of said encapsulates may have a particle wall thickness of from 30 nm to 250 nm, from 80 nm to 180 nm, or even from 100 nm to 160 nm. Formaldehyde scavengers may be employed with encapsulates, for example, in a capsule slurry and/or added to a composition before, during or after the encapsulates are added to such composition. Suitable capsules that can be made by following the teaching of USPA 2008/0305982 A1; and/or USPA 2009/0247449 A1. Alternatively, suitable capsules can be purchased from Appleton Papers Inc. of Appleton, Wis. USA.

In a preferred aspect the composition may comprise a deposition aid, preferably in addition to encapsulates. Preferred deposition aids are selected from the group consisting of cationic and nonionic polymers. Suitable polymers include cationic starches, cationic hydroxyethylcellulose, polyvinylformaldehyde, locust bean gum, mannans, xyloglucans, tamarind gum, polyethyleneterephthalate and polymers containing dimethylaminoethyl methacrylate, optionally with one or more monomers selected from the group comprising acrylic acid and acrylamide.

Perfume. Preferred compositions of the invention comprise perfume. Typically the composition comprises a perfume that comprises one or more perfume raw materials, selected from the group as described in WO08/87497. However, any perfume useful in a laundry care composition may be used. A preferred method of incorporating perfume into the compositions of the invention is via an encapsulated perfume particle comprising either a water-soluble hydroxylic compound or melamine-formaldehyde or modified polyvinyl alcohol.

Malodor Reduction Materials

The cleaning compositions of the present disclosure may comprise malodour reduction materials. Such materials are capable of decreasing or even eliminating the perception of one or more malodors. These materials can be characterized by a calculated malodor reduction value ("MORV"), which is calculated according to the test method shown in WO2016/049389.

As used herein "MORV" is the calculated malodor reduction value for a subject material. A material's MORV indicates such material's ability to decrease or even eliminate the perception of one or more malodors.

The cleaning compositions of the present disclosure may comprise a sum total of from about 0.00025% to about 0.5%, preferably from about 0.0025% to about 0.1%, more preferably from about 0.005% to about 0.075%, most preferably from about 0.01% to about 0.05%, by weight of the composition, of 1 or more malodor reduction materials. The cleaning composition may comprise from about 1 to about 20 malodor reduction materials, more preferably 1 to about 15 malodor reduction materials, most preferably 1 to about 10 malodor reduction materials.

One, some, or each of the malodor reduction materials may have a MORV of at least 0.5, preferably from 0.5 to 10, more preferably from 1 to 10, most preferably from 1 to 5. One, some, or each of the malodor reduction materials may have a Universal MORV, defined as all of the MORV values of >0.5 for the malodors tested as described herein. The sum total of malodor reduction materials may have a Blocker Index of less than 3, more preferable less than about 2.5, even more preferably less than about 2, and still more preferably less than about 1, and most preferably about 0. The sum total of malodor reduction materials may have a Blocker Index average of from about 3 to about 0.001.

In the cleaning compositions of the present disclosure, the malodor reduction materials may have a Fragrance Fidelity Index of less than 3, preferably less than 2, more preferably less than 1 and most preferably about 0 and/or a Fragrance Fidelity Index average of 3 to about 0.001 Fragrance Fidelity Index. As the Fragrance Fidelity Index decreases, the malodor reduction material(s) provide less and less of a scent impact, while continuing to counteract malodors.

The cleaning compositions of the present disclosure may comprise a perfume. The weight ratio of parts of malodor reduction composition to parts of perfume may be from about 1:20,000 to about 3000:1, preferably from about 1:10,000 to about 1,000:1, more preferably from about 5,000:1 to about 500:1, and most preferably from about 1:15 to about 1:1. As the ratio of malodor reduction composition to parts of perfume is tightened, the malodor reduction material(s) provide less and less of a scent impact, while continuing to counteract malodors.

Tannins

The cleaning compositions of the present disclosure may comprise tannins Tannins are polyphenolic secondary metabolites of higher plants, and are either galloyl esters and their derivatives, in which galloyl moieties or their derivatives are attached to a variety of polyol-, catechin- and triterpenoid cores (gallotannins, ellagitannins and complex tannins), or they are oligomeric and polymeric proanthocyanidis that can possess interflavanyl coupling and substitution patterns (condensed tannins). The cleaning compositions of the present disclosure may comprise tannins selected from the group consisting of gallotannins, ellagitannins, complex tannins, condensed tannins, and combinations thereof Polymers. The composition may comprise one or more polymers. Examples are optionally modified carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The composition may comprise one or more amphiphilic cleaning polymers. Such polymers have balanced hydrophilic and hydrophobic properties such that they remove grease particles from fabrics and surfaces. Suitable amphiphilic alkoxylated grease cleaning polymers comprise a core structure and a plurality of alkoxylate groups attached to that core structure. These may comprise alkoxylated polyalkylenimines, especially ethoxylated polyethylene imines or polyethyleneimines having an inner polyethylene oxide block and an outer polypropylene oxide block. Typically these may be incorporated into the compositions of the invention in amounts of from 0.005 to 10 wt %, generally from 0.5 to 8 wt %.

The composition may comprise a modified hexamethylenediamine. The modification of the hexamethylenediamine includes: (1) one or two alkoxylation modifications per nitrogen atom of the hexamethylenediamine. The alkoxylation modification consisting of the replacement of a hydrogen atom on the nitrogen of the hexamethylenediamine by a (poly)alkoxylene chain having an average of about 1 to about 40 alkoxy moieties per modification, wherein the terminal alkoxy moiety of the alkoxylene chain is capped with hydrogen, a C1-C4 alkyl, sulfates, carbonates, or mixtures thereof; (2) a substitution of one C1-C4 alkyl moiety and one or two alkoxylation modifications per nitrogen atom of the hexamethylenediamine. The alkoxylation modification consisting of the replacement of a hydrogen atom by a (poly)alkoxylene chain having an average of about 1 to about 40 alkoxy moieties per modification wherein the terminal alkoxy moiety of the alkoxylene chain is capped with hydrogen, a C1-C4 alkyl or mixtures thereof; or (3) a combination thereof Alkoxylated polycarboxylates such as those prepared from polyacrylates are useful herein to provide additional grease removal performance Such materials are described in WO 91/08281 and PCT 90/01815. Chemically, these materials comprise polyacrylates having one ethoxy side-chain per every 7-8 acrylate units. The side-chains are of the formula —$(CH_2CH_2O)_m(CH_2)_nCH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

Another suitable carboxylate polymer is a co-polymer that comprises: (i) from 50 to less than 98 wt % structural units derived from one or more monomers comprising carboxyl groups; (ii) from 1 to less than 49 wt % structural units derived from one or more monomers comprising sulfonate moieties; and (iii) from 1 to 49 wt % structural units derived from one or more types of monomers selected from ether bond-containing monomers represented by formulas (I) and (II):

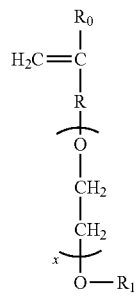

formula (I)

wherein in formula (I), $R_0$ represents a hydrogen atom or $CH_3$ group, R represents a $CH_2$ group, $CH_2CH_2$ group or single bond, X represents a number 0-5 provided X represents a number 1-5 when R is a single bond, and $R_1$ is a hydrogen atom or $C_1$ to $C_{20}$ organic group;

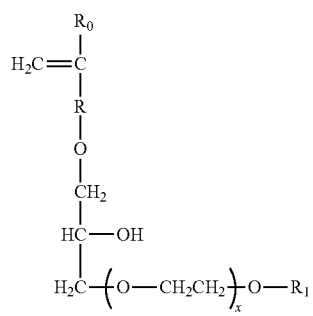

formula (II)

wherein in formula (II), $R_0$ represents a hydrogen atom or $CH_3$ group, R represents a $CH_2$ group, $CH_2CH_2$ group or single bond, X represents a number 0-5, and $R_1$ is a hydrogen atom or $C_1$ to $C_{20}$ organic group.

It may be preferred that the polymer has a weight average molecular weight of at least 50 kDa, or even at least 70 kDa.

Other suitable polymers include amphiphilic graft copolymers. Preferred amphiphilic graft co-polymer(s) comprise (i) polyetheylene glycol backbone; and (ii) and at least one pendant moiety selected from polyvinyl acetate, polyvinyl alcohol and mixtures thereof. A preferred amphiphilic graft co-polymer is Sokalan HP22, supplied from BASF. Other suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is preferably about 6000 and the weight ratio of the polyethylene oxide to polyvinyl acetate is about 40 to 60 and no more than 1 grafting point per 50 ethylene oxide units. Typically these are incorporated into the compositions of the invention in amounts from 0.005 to 10 wt %, more usually from 0.05 to 8 wt %.

The composition may comprise one or more soil release polymers. Examples include soil release polymers having a structure as defined by one of the following Formula (VI), (VII) or (VIII):

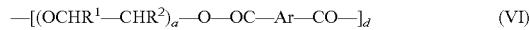  (VI)

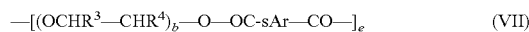  (VII)

  (VIII)

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
$R^1$, $R^2$, $R^3$, $R^4$, $R^5$ and $R^6$ are independently selected from H or $C_1$-$C_{18}$ n- or iso-alkyl; and
$R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.

The composition may also comprise one or more cellulosic polymer, including those selected from alkyl cellulose, alkyl alkoxyalkyl cellulose, carboxyalkyl cellulose, alkyl carboxyalkyl cellulose. Preferred cellulosic polymers are selected from the group comprising carboxymethyl cellulose, methyl cellulose, methyl hydroxyethyl cellulose, methyl carboxymethyl cellulose, and mixures thereof. In one aspect, the carboxymethyl cellulose has a degree of carboxymethyl substitution from 0.5 to 0.9 and a molecular weight from 100,000 Da to 300,000 Da.

Soil release polymer: The composition may comprise a soil release polymer. A suitable soil release polymer has a structure as defined by one of the following structures (I), (II) or (III):

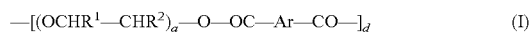
$$-[(OCHR^1-CHR^2)_a-O-OC-Ar-CO-]_d \quad (I)$$

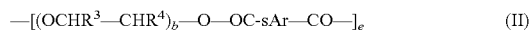
$$-[(OCHR^3-CHR^4)_b-O-OC-sAr-CO-]_e \quad (II)$$

$$-[(OCHR^5-CHR^6)_c-OR^7]_f \quad (III)$$

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
$R^1$, $R^2$, $R^3$, $R^4$, $R^5$ and $R^6$ are independently selected from H or $C_1$-$C_{18}$ n- or iso-alkyl; and
$R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are sold by Clariant under the TexCare® series of polymers, e.g. TexCare® SRN240 and TexCare® SRA300. Other suitable soil release polymers are sold by Solvay under the Repel-o-Tex® series of polymers, e.g. Repel-o-Tex® SF2 and Repel-o-Tex® Crystal.

Known polymeric soil release agents, hereinafter "SRA" or "SRA's", can optionally be employed in the present detergent compositions. If utilized, SRA's will generally comprise from 0.01% to 10.0%, typically from 0.1% to 5%, preferably from 0.2% to 3.0% by weight, of the composition.

Preferred SRA's typically have hydrophilic segments to hydrophilize the surface of hydrophobic fibers such as polyester and nylon, and hydrophobic segments to deposit upon hydrophobic fibers and remain adhered thereto through completion of washing and rinsing cycles thereby serving as an anchor for the hydrophilic segments. This can enable stains occurring subsequent to treatment with SRA to be more easily cleaned in later washing procedures.

SRA's can include, for example, a variety of charged, e.g., anionic or even cationic (see U.S. Pat. No. 4,956,447), as well as noncharged monomer units and structures may be linear, branched or even star-shaped. They may include capping moieties which are especially effective in controlling molecular weight or altering the physical or surface-active properties. Structures and charge distributions may be tailored for application to different fiber or textile types and for varied detergent or detergent additive products. Suitable soil release polymers are polyester soil release polymers such as Repel-o-tex polymers, including Repel-o-tex, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol Examples of SRAs are described in U.S. Pat. Nos. 4,968,451; 4,711,730; 4,721,580; 4,702,857; 4,877,896; 3,959,230; 3,893,929; 4,000,093; 5,415,807; 4,201,824; 4,240,918; 4,525,524; 4,201,824; 4,579,681; and 4,787,989; European Patent Application 0 219 048; 279,134 A; 457,205 A; and DE 2,335,044.

Carboxylate polymer: The composition may comprise a carboxylate polymer, such as a maleate/acrylate random copolymer or polyacrylate homopolymer. Suitable carboxylate polymers include: polyacrylate homopolymers having a molecular weight of from 4,000 Da to 9,000 Da; maleate/acrylate random copolymers having a molecular weight of from 50,000 Da to 100,000 Da, or from 60,000 Da to 80,000 Da.

Alternatively, these materials may comprise polyacrylates having one ethoxy side-chain per every 7-8 acrylate units. The side-chains are of the formula $-(CH_2CH_2O)_m(CH_2)_n CH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

Another suitable carboxylate polymer is a co-polymer that comprises: (i) from 50 to less than 98 wt % structural units derived from one or more monomers comprising carboxyl groups; (ii) from 1 to less than 49 wt % structural units derived from one or more monomers comprising sulfonate moieties; and (iii) from 1 to 49 wt % structural units derived from one or more types of monomers selected from ether bond-containing monomers represented by formulas (I) and (II):

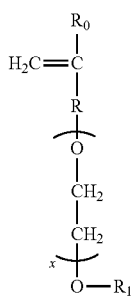

formula (I)

wherein in formula (I), $R_0$ represents a hydrogen atom or $CH_3$ group, R represents a $CH_2$ group, $CH_2CH_2$ group or single bond, X represents a number 0-5 provided X represents a number 1-5 when R is a single bond, and $R_1$ is a hydrogen atom or $C_1$ to $C_{20}$ organic group;

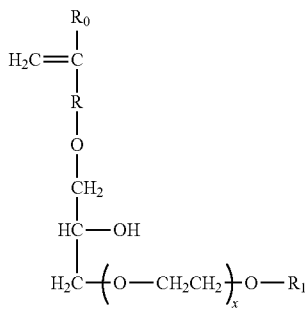

formula (II)

wherein in formula (II), $R_0$ represents a hydrogen atom or $CH_3$ group, R represents a $CH_2$ group, $CH_2CH_2$ group or single bond, X represents a number 0-5, and $R_1$ is a hydrogen atom or $C_1$ to $C_{20}$ organic group.

It may be preferred that the polymer has a weight average molecular weight of at least 50 kDa, or even at least 70 kDa.

Such carboxylate based polymers can advantageously be utilized at levels from about 0.1% to about 7%, by weight, in the compositions herein. Suitable polymeric dispersing agents include carboxylate polymer such as a maleate/acrylate random copolymer or polyacrylate homopolymer. Preferably the carboxylate polymer is a polyacrylate homopolymer having a molecular weight of from 4,000 Daltons to 9,000 Daltons, or maleate/acrylate copolymer with a molecular weight 60,000 Daltons to 80,000 Daltons. Polymeric polycarboxylates and polyethylene glycols, can also be used. Polyalkylene glycol-based graft polymer may prepared from the polyalkylene glycol-based compound and the monomer material, wherein the monomer material includes the carboxyl group-containing monomer and the optional additional monomer(s). Optional additional monomers not classified as a carboxyl group-containing monomer include sulfonic acid group-containing monomers, amino group-containing monomers, allylamine monomers, quaternized allylamine monomers, N vinyl monomers, hydroxyl group-containing monomers, vinylaryl monomers, isobutylene monomers, vinyl acetate monomers, salts of any of these, derivatives of any of these, and mixtures thereof. It is believed, though it is not intended to be limited by theory, that polymeric dispersing agents enhance overall detergent builder performance, when used in combination with other builders (including lower molecular weight polycarboxy-lates) by crystal growth inhibition, particulate soil release peptization, and anti-redeposition. Examples of polymeric dispersing agents are found in U.S. Pat. No. 3,308,067, European Patent Application No. 66915, EP 193,360, and EP 193,360.

Alkoxylated polyamine based polymers: The composition may comprisse alkoxylated polyamines Such materials include but are not limited to ethoxylated polyethyleneimine, ethoxylated hexamethylene diamine, and sulfated versions thereof. Polypropoxylated derivatives are also included. A wide variety of amines and polyaklyeneimines can be alkoxylated to various degrees, and optionally further modified to provide the abovementioned benefits. A useful example is 600 g/mol polyethyleneimine core ethoxylated to 20 EO groups per NH and is available from BASF.

Useful alkoxylated polyamine based polymers include the alkoxylated polyethylene imine type where said alkoxylated polyalkyleneimine has a polyalkyleneimine core with one or more side chains bonded to at least one nitrogen atom in the polyalkyleneimine core, wherein said alkoxylated polyalkyleneimine has an empirical formula (I) of $(PEI)_a-(EO)_b-R_1$, wherein a is the average number-average molecular weight ($MWp_{PE1}$) of the polyalkyleneimine core of the alkoxylated polyalkyleneimine and is in the range of from 100 to 100,000 Daltons, wherein b is the average degree of ethoxylation in said one or more side chains of the alkoxylated polyalkyleneimine and is in the range of from 5 to 40, and wherein $R_1$ is independently selected from the group consisting of hydrogen, $C_1$-$C_4$ alkyls, and combinations thereof.

Other suitable alkoxylated polyalkyleneimine incldue those wherein said alkoxylated polyalkyleneimine has a polyalkyleneimine core with one or more side chains bonded to at least one nitrogen atom in the polyalkyleneimine core, wherein the alkoxylated polyalkyleneimine has an empirical formula (II) of $(PEI)_o-(EO)_m(PO)_n-R_2$ or $(PEI)_o-(PO)_n(EO)_m-R_2$, wherein o is the average number-average molecular weight ($MW_{PEI}$) of the polyalkyleneimine core of the alkoxylated polyalkyleneimine and is in the range of from 100 to 100,000 Daltons, wherein m is the average degree of ethoxylation in said one or more side chains of the alkoxylated polyalkyleneimine which ranges from 10 to 50, wherein n is the average degree of propoxylation in said one or more side chains of the alkoxylated polyalkyleneimine which ranges from 1 to 50, and wherein $R_2$ is independently selected from the group consisting of hydrogen, $C_1$-$C_4$ alkyls, and combinations thereof.

Amphiphilic graft co-polymer—Amphiphilic graft copolymer may also be used according to the invention. Especially useful polymers include those comprising (i) polyethyelene glycol backbone; and (ii) and at least one pendant moiety selected from polyvinyl acetate, polyvinyl alcohol and mixtures thereof are also useful in the present invention. Suitable polyethylene glycol polymers include random graft co-polymers comprising: (i) hydrophilic backbone comprising polyethylene glycol; and (ii) hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Suitable polyethylene glycol polymers are described in WO08/007320.

Cellulosic polymer: Cellulosic polymers may be used according to the invention. Suitable cellulosic polymers are selected from alkyl cellulose, alkyl alkoxyalkyl cellulose, carboxyalkyl cellulose, alkyl carboxyalkyl cellulose, sulphoalkyl cellulose, more preferably selected from carboxymethyl cellulose, methyl cellulose, methyl hydroxyethyl cellulose, methyl carboxymethyl cellulose, and mixures thereof.

Suitable carboxymethyl celluloses have a degree of carboxymethyl substitution from 0.5 to 0.9 and a molecular weight from 100,000 Da to 300,000 Da.

Suitable carboxymethyl celluloses have a degree of substitution greater than 0.65 and a degree of blockiness greater than 0.45, e.g. as described in WO09/154933.

The consumer products of the present invention may also include one or more cellulosic polymers including those selected from alkyl cellulose, alkylalkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 Da to 300,000 Da. Examples of carboxymethylcellulose polymers are Carboxymethyl cellulose commercially sold by CPKelko as Finnfix®GDA, hydrophobically modified carboxymethyl cellulose, for example the alkyl ketene dimer derivative of carboxymethylcellulose sold commercially by CPKelco as Finnfix®SH1, or the blocky carboxymethylcellulose sold commercially by CPKelco as Finnfix®V.

Cationic Polymers: Cationic polymers may also be used according to the invention. Suitable cationic polymers will have cationic charge densities of at least 0.5 meq/gm, in another embodiment at least 0.9 meq/gm, in another embodiment at least 1.2 meq/gm, in yet another embodiment at least 1.5 meq/gm, but in one embodiment also less than 7 meq/gm, and in another embodiment less than 5 meq/gm, at the pH of intended use of the composition, which pH will generally range from pH 3 to pH 9, in one embodiment between pH 4 and pH 8. Herein, "cationic charge density" of a polymer refers to the ratio of the number of positive charges on the polymer to the molecular weight of the polymer. The average molecular weight of such suitable cationic polymers will generally be between 10,000 and 10 million, in one embodiment between 50,000 and 5 million, and in another embodiment between 100,000 and 3 million.

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Nonlimiting examples of such counterions include halides (e.g., chloride, fluoride, bromide, iodide), sulfate and methylsulfate.

Nonlimiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Especially useful cationic polymers which may be used according to the invention include wherein said cationic polymer comprises a polymer selected from the group consisting of cationic celluloses, cationic guars, poly(acrylamide-co-diallyldimethylammonium chloride), poly(acrylamide-co-diallyldimethylammonium chloride-co-acrylic acid), poly(acrylamide-co-methacryloamidopropyl-pentamethyl-1,3-propylene-2-ol-ammonium dichloride), poly(acrylamide-co-N,N-dimethylaminoethyl acrylate) and its quaternized derivatives, poly(acrylamide-co-N,N-dimethylaminoethyl methacrylate) and its quaternized derivatives, poly(acrylamide-methacrylamidopropyltrimethyl ammonium chloride), poly(acrylamide-methacrylamidopropyltrimethyl ammonium chloride-co-acrylic acid), poly(diallyldimethyl ammonium chloride), poly(diallyldimethylammonium chloride-co-acrylic acid), poly(ethyl methacrylate-co-oleyl methacrylate-co-diethylaminoethyl methacrylate) and its quaternized derivatives, poly(ethyl methacrylate-co-dimethylaminoethyl methacrylate) and its quaternized derivatives, poly(hydroxpropylacrylate-co-methacrylamidopropyltrimethylammonium chloride) and its quaternized derivatives, poly(hydroxyethylacrylate-co-dimethyl aminoethyl methacrylate) and its quaternized derivatives, poly(methylacrylamide-co-dimethylaminoethyl acrylate) and its quaternized derivatives, poly(methacrylate-co-methacrylamidopropyltrimethyl ammonium chloride), poly (vinylformamide-co-acrylic acid-co-diallyldimethylammonium chloride), poly(vinylformamide-co-diallyldimethylammonium chloride), poly(vinylpyrrolidone-co-acrylamide-co-vinyl imidazole) and its quaternized derivatives, poly (vinylpyrrolidone-co-dimethylaminoethyl methacrylate) and its quaternized derivatives, poly(vinylpyrrolidone-co-methacrylamide-co-vinyl imidazole) and its quaternized derivatives, poly(vinylpyrrolidone-co-vinyl imidazole) and its quaternized derivatives, polyethyleneimine and including its quaternized derivatives, and mixtures thereof Other suitable cationic polymers for use in the composition include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Complex coacervates of the cationic polymer can also be formed with other charged materials in the composition.

Suitable cationic polymers are described in U.S. Pat. Nos. 3,962,418; 3,958,581; and U.S. Publication No. 2007/0207109A1.

Dye Transfer Inhibitor (DTI). The composition may comprise one or more dye transfer inhibiting agents. In one embodiment of the invention the inventors have surprisingly found that compositions comprising polymeric dye transfer inhibiting agents in addition to the specified dye give improved performance. This is surprising because these polymers prevent dye deposition. Suitable dye transfer inhibitors include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Suitable examples include PVP-K15, PVP-K30, ChromaBond S-400, ChromaBond S-403E and Chromabond S-100 from Ashland Aqualon, and Sokalan HP165, Sokalan HP50, Sokalan HP53, Sokalan HP59, Sokalan® HP 56K, Sokalan® HP 66 from BASF. The dye control agent may be selected from (i) a sulfonated phenol/formaldehyde polymer; (ii) a urea derivative; (iii) polymers of ethylenically unsaturated monomers, where the polymers are molecularly imprinted with dye; (iv) fibers consisting of water-insoluble polyamide, wherein the fibers have an average diameter of not more than about 2 μm; (v) a polymer obtainable from polymerizing benzoxazine monomer compounds; and (vi) combinations thereof. Other suitable DTIs are as described in WO2012/004134. When present in a subject composition, the dye transfer inhibiting agents may be present at levels from about 0.0001% to about 10%, from about 0.01% to about 5% or even from about 0.1% to about 3% by weight of the composition.

Other water soluble polymers: Examples of water soluble polymers include but are not limited to polyvinyl alcohols (PVA), modified PVAs; polyvinyl pyrrolidone; PVA copolymers such as PVA/polyvinyl pyrrolidone and PVA/polyvinyl amine; partially hydrolyzed polyvinyl acetate; polyalkylene oxides such as polyethylene oxide; polyethylene glycols; acrylamide; acrylic acid; cellulose, alkyl cellulosics such as methyl cellulose, ethyl cellulose and propyl cellulose; cellulose ethers; cellulose esters; cellulose amides; polyvinyl acetates; polycarboxylic acids and salts; polyaminoacids or peptides; polyamides; polyacrylamide; copolymers of maleic/acrylic acids; polysaccharides including starch, modified starch; gelatin; alginates; xyloglucans, other hemicellulosic polysaccharides including xylan, glucuronoxylan, arabinoxylan, mannan, glucomannan and galactoglucomannan; and natural gums such as pectin, xanthan, and carrageenan, locus bean, arabic, tragacanth; and combinations thereof Non-limiting examples of amines include, but are not limited to, etheramines, cyclic amines, polyamines, oligoamines (e.g., triamines, diamines, pentamines, tetraamines), or combinations thereof. The compositions described herein may comprise an amine selected from the group consisting of oligoamines, etheramines, cyclic amines, and combinations thereof. In some aspects, the amine is not an alkanolamine. In some aspects, the amine is not a polyalkyleneimine.

Examples of suitable oligoamines include tetraethylenepentamine, triethylenetetraamine, diethylenetriamine, and mixtures thereof.

Etheramines: The cleaning compositions described herein may contain an etheramine. The cleaning compositions may contain from about 0.1% to about 10%, or from about 0.2% to about 5%, or from about 0.5% to about 4%, by weight of the composition, of an etheramine.

The etheramines of the present disclosure may have a weight average molecular weight of less than about grams/mole 1000 grams/mole, or from about 100 to about 800 grams/mole, or from about 200 to about 450 grams/mole, or from about 290 to about 1000 grams/mole, or from about 290 to about 900 grams/mole, or from about 300 to about 700 grams/mole, or from about 300 to about 450 grams/mole. The etheramines of the present invention may have a weight average molecular weight of from about 150, or from about 200, or from about 350, or from about 500 grams/mole, to about 1000, or to about 900, or to about 800 grams/mole.

Alkoxylated phenol compound: The cleaning compositions of the present disclosure may include an alkoxylated phenol compound. The alkoxylated phenol compound may be selected from the group consisting of an alkoxylated polyaryl phenol compound, an alkoxylated polyalkyl phenol compound, and mixtures thereof. The alkoxylated phenol compound may be an alkoxylated polyaryl phenol compound. The alkoxylated phenol compound may be an alkoxylated polyalkyl phenol compound.

The alkoxylated phenol compound may be present in the cleaning composition at a level of from about 0.2% to about 10%, or from about 0.5% to about 5%, by weight of the cleaning composition.

The alkoxylated phenol compound may have a weight average molecular weight between 280 and 2880.

Enzymes. Preferably the composition comprises one or more enzymes. Preferred enzymes provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in the composition, the aforementioned additional enzymes may be present at levels from about 0.00001% to about 2%, from about 0.0001% to about 1% or even from about 0.001% to about 0.5% enzyme protein by weight of the composition.

Proteases. Preferably the composition comprises one or more proteases. Suitable proteases include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, B. alkalophilus, B. subtilis, B. amyloliquefaciens, Bacillus pumilus* and *Bacillus gibsonii* described in U.S. Pat. Nos. 6,312,936 B1, 5,679,630, 4,760,025, 7,262,042 and WO09/021867.

(b) trypsin-type or chymotrypsin-type proteases, such as trypsin (e.g., of porcine or bovine origin), including the *Fusarium* protease described in WO 89/06270 and the chymotrypsin proteases derived from *Cellumonas* described in WO 05/052161 and WO 05/052146.

(c) metalloproteases, including those derived from *Bacillus amyloliquefaciens* described in WO 07/044993A2.

Preferred proteases include those derived from *Bacillus gibsonii* or *Bacillus Lentus*.

Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark), those sold under the tradename Maxatase®, Maxacal®, Maxapem®, Properase®, Purafect®, Purafect Prime®, Purafect Ox®, FN3®, FN4®, Excellase® and Purafect OXP® by Genencor International, those sold under the tradename Opticlean® and Optimase® by Solvay Enzymes, those available from Henkel/Kemira, namely BLAP (sequence shown in FIG. 29 of U.S. Pat. No. 5,352,604 with the following mutations S99D+S101R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D)—all from Henkel/Kemira; and KAP (*Bacillus alkalophilus subtilisin* with mutations A230V+S256G+S259N) from Kao.

Amylases. Preferably the composition may comprise an amylase. Suitable alpha-amylases include those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis,* or other *Bacillus* sp., such as *Bacillus* sp. NCIB 12289, NCIB 12512, NCIB 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) the variants described in WO 94/02597, WO 94/18314, WO96/23874 and WO 97/43424, especially the variants with substitutions in one or more of the following positions versus the enzyme listed as SEQ ID No. 2 in WO 96/23874: 15, 23, 105, 106, 124, 128, 133, 154, 156, 181, 188, 190, 197, 202, 208, 209, 243, 264, 304, 305, 391, 408, and 444.

(b) the variants described in U.S. Pat. No. 5,856,164 and WO99/23211, WO 96/23873, WO00/60060 and WO 06/002643, especially the variants with one or more substitutions in the following positions versus the AA560 enzyme listed as SEQ ID No. 12 in WO 06/002643:

26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with SEQ ID No. 4 in WO06/002643, the wild-type enzyme from *Bacillus* SP722, especially variants with deletions in the 183 and 184 positions and variants described in WO 00/60060, which is incorporated herein by reference.

(d) variants exhibiting at least 95% identity with the wild-type enzyme from *Bacillus* sp. 707 (SEQ ID NO:7 in U.S. Pat. No. 6,093,562), especially those comprising one or more of the following mutations M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations.

(e) variants described in WO 09/149130, preferably those exhibiting at least 90% identity with SEQ ID NO: 1 or SEQ ID NO:2 in WO 09/149130, the wild-type enzyme from *Geobacillus Stearophermophilus* or a truncated version thereof.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE® and PURASTAR OXAM® (Genencor International Inc., Palo Alto, Calif.) and KAM® (Kao, 14-10 Nihonbashi Kayabacho, 1-chome, Chuo-ku Tokyo 103-8210, Japan). In one aspect, suitable amylases include NATALASE®, STAINZYME® and STAINZYME PLUS® and mixtures thereof.

Lipases. Preferably the invention comprises one or more lipases, including "first cycle lipases" such as those described in U.S. Pat. No. 6,939,702 B1 and US PA 2009/0217464. Preferred lipases are first-wash lipases. In one embodiment of the invention the composition comprises a first wash lipase. First wash lipases includes a lipase which is a polypeptide having an amino acid sequence which: (a) has at least 90% identity with the wild-type lipase derived from *Humicola lanuginosa* strain DSM 4109; (b) compared to said wild-type lipase, comprises a substitution of an electrically neutral or negatively charged amino acid at the surface of the three-dimensional structure within 15A of E1 or Q249 with a positively charged amino acid; and (c) comprises a peptide addition at the C-terminal; and/or (d) comprises a peptide addition at the N-terminal and/or (e) meets the following limitations: i) comprises a negative amino acid in position E210 of said wild-type lipase; ii) comprises a negatively charged amino acid in the region corresponding to positions 90-101 of said wild-type lipase; and iii) comprises a neutral or negative amino acid at a position corresponding to N94 or said wild-type lipase and/or has a negative or neutral net electric charge in the region corresponding to positions 90-101 of said wild-type lipase. Preferred arevariants of the wild-type lipase from *Thermomyces lanuginosus* comprising one or more of the T231R and N233R mutations. The wild-type sequence is the 269 amino acids (amino acids 23-291) of the Swissprot accession number Swiss-Prot O59952 (derived from *Thermomyces lanuginosus* (*Humicola lanuginosa*)). Preferred lipases would include those sold under the tradenames Lipex® and Lipolex® and Lipoclean®.

Endoglucanases. Other preferred enzymes include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403B2) and mixtures thereof. Suitable endoglucanases are sold under the tradenames Celluclean® and Whitezyme® (Novozymes A/S, Bagsvaerd, Denmark).

Pectate Lyases. Other preferred enzymes include pectate lyases sold under the tradenames Pectawash®, Pectaway®, Xpect® and mannanases sold under the tradenames Mannaway® (all from Novozymes A/S, Bagsvaerd, Denmark), and Purabrite® (Genencor International Inc., Palo Alto, Calif.).

Nuclease enzyme. The composition may comprise a nuclease enzyme. The nuclease enzyme is an enzyme capable of cleaving the phosphodiester bonds between the nucleotide sub-units of nucleic acids. The nuclease enzyme herein is preferably a deoxyribonuclease or ribonuclease enzyme or a functional fragment thereof. By functional fragment or part is meant the portion of the nuclease enzyme that catalyzes the cleavage of phosphodiester linkages in the DNA backbone and so is a region of said nuclease protein that retains catalytic activity. Thus it includes truncated, but functional versions, of the enzyme and/or variants and/or derivatives and/or homologues whose functionality is maintained.

Preferably the nuclease enzyme is a deoxyribonuclease, preferably selected from any of the classes E.C. 3.1.21.x, where x=1, 2, 3, 4, 5, 6, 7, 8 or 9, E.C. 3.1.22.y where y=1, 2, 4 or 5, E.C. 3.1.30.z where z=1 or 2, E.C. 3.1.31.1 and mixtures thereof.

Bleaching Agents. It may be preferred for the composition to comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the compositions of the present invention may comprise from about 0.1% to about 50% or even from about 0.1% to about 25% bleaching agent or mixtures of bleaching agents by weight of the subject composition. Examples of suitable bleaching agents include:

(1) photobleaches for example sulfonated zinc phthalocyanine sulfonated aluminium phthalocyanines, xanthene dyes, thioxanthones, and mixtures thereof;

(2) pre-formed peracids: Suitable preformed peracids include, but are not limited to compounds selected from the group consisting of pre-formed peroxyacids or salts thereof typically a percarboxylic acids and salts, percarbonic acids and salts, perimidic acids and salts, peroxymonosulfuric acids and salts, for example, Oxone®, and mixtures thereof.

Particularly preferred peroxyacids are phthalimido-peroxy-alkanoic acids, in particular ε-phthalimido peroxy hexanoic acid (PAP). Preferably, the peroxyacid or salt thereof has a melting point in the range of from 30° C. to 60° C.

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. When employed, inorganic perhydrate salts are typically present in amounts of from 0.05 to 40 wt %, or 1 to 30 wt % of the overall fabric and home care product and are typically incorporated into such fabric and home care products as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof— especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS).

(5) Bleach Catalysts. The compositions of the present invention may also include one or more bleach catalysts capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and alpha amino-ketones and mixtures thereof. One particularly preferred catalyst is acyl hydrazone type such as 4-(2-(2-((2-hydroxyphenylmethyl)methylene)-hydrazinyl)-2-oxoethyl)-4-methylchloride.

(6) The composition may preferably comprise catalytic metal complexes. One preferred type of metal-containing bleach catalyst is a catalyst system comprising a transition metal cation of defined bleach catalytic activity, such as copper, iron, titanium, ruthenium, tungsten, molybdenum, or manganese cations.

If desired, the compositions herein can be catalyzed by means of a manganese compound. Such compounds and levels of use are well known in the art and include, for example, the manganese-based catalysts disclosed in U.S. Pat. No. 5,576,282. In some embodiments, an additional source of oxidant in the composition is not present, molecular oxygen from air providing the oxidative source.

Cobalt bleach catalysts useful herein are known, and are described, for example, in U.S. Pat. Nos. 5,597,936; and 5,595,967.

When present, the source of hydrogen peroxide/peracid and/or bleach activator is generally present in the composition in an amount of from about 0.1 to about 60 wt %, from about 0.5 to about 40 wt % or even from about 0.6 to about 10 wt % based on the fabric and home care product. One or more hydrophobic peracids or precursors thereof may be used in combination with one or more hydrophilic peracid or precursor thereof.

Typically hydrogen peroxide source and bleach activator will be incorporated together. The amounts of hydrogen peroxide source and peracid or bleach activator may be selected such that the molar ratio of available oxygen (from the peroxide source) to peracid is from 1:1 to 35:1, or even 2:1 to 10:1. If formulated into a liquid detergent, the peroxide source and activator may be formulated at low pH, typically 3-5 together with a pH jump system such as borate/sorbitol.

The laundry care compositions of the present invention may be especially used in chlorinated water such as typically found in most domestic water supplies. Alternatively the leuco comprising systems may be used in conjunction with other sources of bleaching such as electrolysis and may be used in an autodosed system.

Builders. Preferably the composition may comprise one or more builders or a builder system. When a builder is used, the composition of the invention will typically comprise at least 1%, from 2% to 60% builder. It may be preferred that the composition comprises low levels of phosphate salt and/or zeolite, for example from 1 to 10 or 5 wt %. The composition may even be substantially free of strong builder; substantially free of strong builder means "no deliberately added" zeolite and/or phosphate. Typical zeolite builders include zeolite A, zeolite P and zeolite MAP. A typical phosphate builder is sodium tri-polyphosphate.

Chelating Agent. Preferably the composition comprises chelating agents and/or crystal growth inhibitor. Suitable molecules include copper, iron and/or manganese chelating agents and mixtures thereof. Suitable molecules include hydroxamic acids, aminocarboxylates, aminophosphonates, succinates, salts thereof, and mixtures thereof. Non-limiting examples of suitable chelants for use herein include ethylenediaminetetracetates, N-(hydroxyethyl)ethylenediaminetriacetates, nitrilotriacetates, ethylenediamine tetrapropionates, triethylenetetraaminehexacetates, diethylenetriamine-pentaacetates, ethanoldiglycines, ethylenediaminetetrakis (methylenephosphonates), diethylenetriamine penta (methylene phosphonic acid) (DTPMP), ethylenediamine disuccinate (EDDS), hydroxyethanedimethylenephosphonic acid (HEDP), methylglycinediacetic acid (MGDA), diethylenetriaminepentaacetic acid (DTPA), salts thereof, and mixtures thereof. Other nonlimiting examples of chelants of use in the present invention are found in U.S. Pat. Nos. 7,445,644, 7,585,376 and 2009/0176684A1. Other suitable chelating agents for use herein are the commercial DEQUEST series, and chelants from Monsanto, DuPont, and Nalco, Inc. Yet other suitable chelants include the pyridinyl N Oxide type Fluorescent Brightener. Preferably the composition comprises one or more fluorescent brightener. Commercial optical brighteners which may be useful in the present invention can be classified into subgroups, which include, but are not limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Particularly preferred brighteners are selected from: sodium 2 (4-styryl-3-sulfophenyl)-2H-napthol [1,2-d]triazole, disodium 4,4'-bis{[(4-anilino-6-(N methyl-N-2 hydroxyethyl) amino 1,3,5-triazin-2-yl)] amino}stilbene-2-2-disulfonate, disodium 4,4'-bis{[(4-anilino-6-morpholino-1,3,5-triazin-2-yl)]amino}stilbene-2-2' disulfonate, and disodium 4,4'-bis (2-sulfostyryl) biphenyl. Other examples of such brighteners are disclosed in "The Production and Application of Fluorescent Brightening Agents", M. Zahradnik, Published by John Wiley & Sons, New York (1982). Specific nonlimiting examples of optical brighteners which are useful in the present compositions are those identified in U.S. Pat. Nos. 4,790,856 and 3,646,015.

A preferred brightener has the structure below:

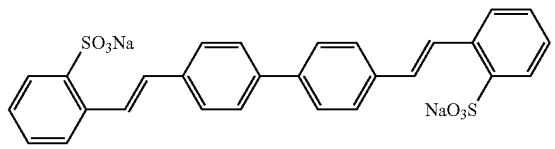

Suitable fluorescent brightener levels include lower levels of from about 0.01, from about 0.05, from about 0.1 or even from about 0.2 wt % to upper levels of 0.5 or even 0.75 wt %.

In one aspect the brightener may be loaded onto a clay to form a particle.

Preferred brighteners are totally or predominantly (typically at least 50 wt %, at least 75 wt %, at least 90 wt %, at least 99 wt %), in alpha-crystalline form. A highly preferred brightener comprises C.I. fluorescent brightener 260, preferably having the following structure:

Enzyme Stabilizers. The composition may preferably comprise enzyme stabilizers. Any conventional enzyme stabilizer may be used, for example by the presence of water-soluble sources of calcium and/or magnesium ions in the finished fabric and home care products that provide such ions to the enzymes. In case of aqueous compositions comprising protease, a reversible protease inhibitor, such as a boron compound including borate, or preferably 4-formyl phenylboronic acid, phenylboronic acid and derivatives thereof, or compounds such as calcium formate, sodium formate and 1,2-propane diol can be added to further improve stability.

Solvent System. The solvent system in the present compositions can be a solvent system containing water alone or mixtures of organic solvents either without or preferably with water.

Organic Solvents

The compositions may optionally comprise an organic solvent. Suitable organic solvents include $C_{4-14}$ ethers and diethers, glycols, alkoxylated glycols, $C_6$-$C_{16}$ glycol ethers, alkoxylated aromatic alcohols, aromatic alcohols, aliphatic branched alcohols, alkoxylated aliphatic branched alcohols, alkoxylated linear $C_1$-$C_5$ alcohols, linear $C_1$-$C_5$ alcohols, amines, $C_8$-$C_{14}$ alkyl and cycloalkyl hydrocarbons and halohydrocarbons, and mixtures thereof. Preferred organic solvents include 1,2-propanediol, 2,3 butane diol, ethanol, glycerol, ethoxylated glycerol, dipropylene glycol, methyl propane diol and mixtures thereof. Other lower alcohols, C1-C4 alkanolamines such as monoethanolamine and triethanolamine, can also be used. Solvent systems can be absent, for example from anhydrous solid embodiments of the invention, but more typically are present at levels in the range of from about 0.1% to about 98%, preferably at least about 1% to about 50%, more usually from about 5% to about 25%, alternatively from about 1% to about 10% by weight of the liquid detergent composition of said organic solvent. These organic solvents may be used in conjunction with water, or they may be used without water Structured Liquids: In some embodiments of the invention, the composition is in the form of a structured liquid. Such structured liquids can either be internally structured, whereby the structure is formed by primary ingredients (e.g. surfactant material) and/or externally structured by providing a three dimensional matrix structure using secondary ingredients (e.g. polymers, clay and/or silicate material), for use e.g. as thickeners. The composition may comprise a structurant, preferably from 0.01 wt % to 5 wt %, from 0.1 wt % to 2.0 wt % structurant. Examples of suitable structurants are given in US2006/0205631A1, US2005/

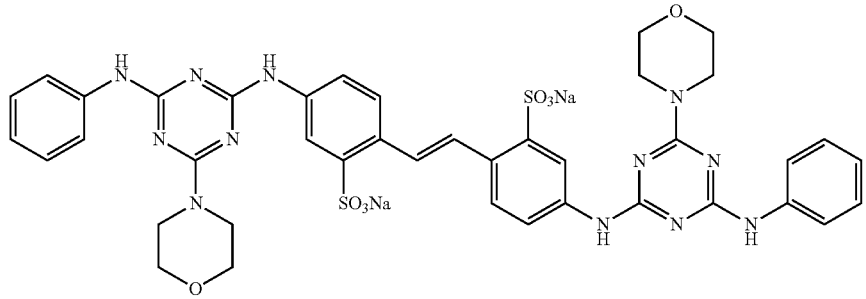

This can be particularly useful as it dissolves well in cold water, for example below 30° C. or 25° C. or even 20° C.

0203213A1, U.S. Pat. Nos. 7,294,611, and 6,855,680. The structurant is typically selected from the group consisting of diglycerides and triglycerides, ethylene glycol distearate, microcrystalline cellulose, cellulose-based materials, microfiber cellulose, hydrophobically modified alkali-swellable emulsions such as Polygel W30 (3VSigma), biopolymers, xanthan gum, gellan gum, hydrogenated castor oil, derivatives of hydrogenated castor oil such as non-ethoxylated derivatives thereof and mixtures thereof, in particular, those selected from the group of hydrogenated castor oil, derivatives of hydrogenated castor oil, microfibullar cellulose, hydroxyfunctional crystalline materials, long chain fatty alcohols, 12-hydroxystearic acids, clays and mixtures thereof. One preferred structurant is described in U.S. Pat. No. 6,855,680 which defines suitable hydroxyfunctional crystalline materials in detail. Preferred is hydrogenated castor oil. Some structurants have a thread-like structuring system having a range of aspect ratios. Another preferred structurant is based on cellulose and may be derived from a number of sources including biomass, wood pulp, citrus fibers and the like.

The composition of the present invention may comprise a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992. When present, the high melting point fatty compound is preferably included in the composition at a level of from 0.1% to 40%, preferably from 1% to 30%, more preferably from 1.5% to 16% by weight of the composition, from 1.5% to 8% in view of providing improved conditioning benefits such as slippery feel during the application to wet hair, softness and moisturized feel on dry hair.

Cationic Polymer. The compositions of the present invention may contain a cationic polymer. Concentrations of the cationic polymer in the composition typically range from 0.05% to 3%, in another embodiment from 0.075% to 2.0%, and in yet another embodiment from 0.1% to 1.0%. Suitable cationic polymers will have cationic charge densities of at least 0.5 meq/gm, in another embodiment at least 0.9 meq/gm, in another embodiment at least 1.2 meq/gm, in yet another embodiment at least 1.5 meq/gm, but in one embodiment also less than 7 meq/gm, and in another embodiment less than 5 meq/gm, at the pH of intended use of the composition, which pH will generally range from pH 3 to pH 9, in one embodiment between pH 4 and pH 8. Herein, "cationic charge density" of a polymer refers to the ratio of the number of positive charges on the polymer to the molecular weight of the polymer. The average molecular weight of such suitable cationic polymers will generally be between 10,000 and 10 million, in one embodiment between 50,000 and 5 million, and in another embodiment between 100,000 and 3 million.

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Nonlimiting examples of such counterions include halides (e.g., chloride, fluoride, bromide, iodide), sulfate and methylsulfate.

Nonlimiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Other suitable cationic polymers for use in the composition include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Complex coacervates of the cationic polymer can also be formed with other charged materials in the composition.

Suitable cationic polymers are described in U.S. Pat. Nos. 3,962,418; 3,958,581; and U.S. Publication No. 2007/0207109A1.

Nonionic Polymer. The composition of the present invention may include a nonionic polymer as a conditioning agent. Polyalkylene glycols having a molecular weight of more than 1000 are useful herein. Useful are those having the following general formula:

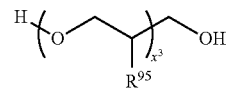

wherein $R^{95}$ is selected from the group consisting of H, methyl, and mixtures thereof.

Conditioning agents, and in particular silicones, may be included in the composition. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits. Such concentration can vary with the conditioning agent, the conditioning performance desired, the average size of the conditioning agent particles, the type and concentration of other components, and other like factors.

The concentration of the silicone conditioning agent typically ranges from about 0.01% to about 10%. Non-limiting examples of suitable silicone conditioning agents, and optional suspending agents for the silicone, are described in U.S. Reissue Pat. No. 34,584, U.S. Pat. Nos. 5,104,646; 5,106,609; 4,152,416; 2,826,551; 3,964,500; 4,364,837; 6,607,717; 6,482,969; 5,807,956; 5,981,681; 6,207,782; 7,465,439; 7,041,767; 7,217,777; US Patent Application Nos. 2007/0286837A1; 2005/0048549A1; 2007/

0041929A1; British Pat. No. 849,433; German Patent No. DE 10036533, which are all incorporated herein by reference; Chemistry and Technology of Silicones, New York: Academic Press (1968); General Electric Silicone Rubber Product Data Sheets SE 30, SE 33, SE 54 and SE 76; Silicon Compounds, Petrarch Systems, Inc. (1984); and in Encyclopedia of Polymer Science and Engineering, vol. 15, 2d ed., pp 204-308, John Wiley & Sons, Inc. (1989).

Organic Conditioning Oil. The compositions of the present invention may also comprise from about 0.05% to about 3% of at least one organic conditioning oil as the conditioning agent, either alone or in combination with other conditioning agents, such as the silicones (described herein). Suitable conditioning oils include hydrocarbon oils, polyolefins, and fatty esters. Hygiene Agent. The compositions of the present invention may also comprise components to deliver hygiene and/or malodour benefits such as one or more of zinc ricinoleate, thymol, quaternary ammonium salts such as Bardac®, polyethylenimines (such as Lupasol® from BASF) and zinc complexes thereof, silver and silver compounds, especially those designed to slowly release Ag+ or nano-silver dispersions.

Probiotics. The composition may comprise probiotics, such as those described in WO2009/043709.

Suds Boosters. The composition may preferably comprise suds boosters if high sudsing is desired. Suitable examples are the $C_{10}$-$C_{16}$ alkanolamides or $C_{10}$-$C_{14}$ alkyl sulphates, which are preferably incorporated at 1%-10% levels. The $C_{10}$-$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as $MgCl_2$, $MgSO_4$, $CaCl_2$, $CaSO_4$ and the like, can be added at levels of, typically, 0.1%-2%, to provide additional suds and to enhance grease removal performance.

Suds Suppressor. Compounds for reducing or suppressing the formation of suds may be incorporated into the compositions of the present invention. Suds suppression can be of particular importance in the so-called "high concentration cleaning process" as described in U.S. Pat. Nos. 4,489,455 and 4,489,574, and in front-loading-style washing machines. A wide variety of materials may be used as suds suppressors, and suds suppressors are well known to those skilled in the art. See, for example, Kirk Othmer Encyclopedia of Chemical Technology, Third Edition, Volume 7, pages 430-447 (John Wiley & Sons, Inc., 1979). Examples of suds suppressors include monocarboxylic fatty acid and soluble salts therein, high molecular weight hydrocarbons such as paraffin, fatty acid esters (e.g., fatty acid triglycerides), fatty acid esters of monovalent alcohols, aliphatic C18-C40 ketones (e.g., stearone), N-alkylated amino triazines, waxy hydrocarbons preferably having a melting point below about 100° C., silicone suds suppressors, and secondary alcohols. Particularly useful silicone suds suppressors are based on diphenyl containing silicones.

Silicone suds suppressors are typically utilized in amounts up to 2.0%, by weight, of the detergent composition, although higher amounts may be used.

Pearlescent Agents. Pearlescent agents as described in WO2011/163457 may be incorporated into the compositions of the invention.

The pearlescent agents can be crystalline or glassy solids, transparent or translucent compounds capable of reflecting and refracting light to produce a pearlescent effect. Typically, the pearlescent agents are crystalline particles insoluble in the composition in which they are incorporated. Preferably the pearlescent agents have the shape of thin plates or spheres. Particle size of the pearlescent agent is typically below 200 microns, preferably below 100 microns, more preferably below 50 microns. Inorganic pearlescent agents include aluminosilicates and/or borosilicates. Preferred are the aluminosilicates and/or borosilicates which have been treated to have a very high refractive index, preferably silica, metal oxides, oxychloride coated aluminosilicate and/or borosilicates. More preferred inorganic pearlescent agent is mica, even more preferred titanium dioxide treated mica such as BASF Mearlin Superfine.

The compositions may comprise from 0.005% to 3.0% wt, preferably from 0.01% to 1%, by weight of the composition of the 100% active pearlescent agents. The pearlescent agents may be organic or inorganic. The composition can comprise organic and/or inorganic pearlescent agent.

Organic Pearlescent Agents:

When the composition comprises an organic pearlescent agent, it is comprised at an active level of from 0.05% to 2.0% wt, preferably from 0.1% to 1.0% by weight of the composition of the 100% active organic pearlescent agents. Suitable organic pearlescent agents include monoester and/or diester of alkylene glycols such as ethylene glycol distearate.

Inorganic Pearlescent Agents:

In another embodiment the composition might also comprise an inorganic pearlescent agent. When the composition comprises an inorganic pearlescent agent, it is comprised at an active level of from 0.005% to 1.0% wt, preferably from 0.01% to 0.2% by weight of the composition of the 100% active inorganic pearlescent agents.

Suspension Particles

In one embodiment, the composition further comprises a plurality of suspension particles at a level of from about 0.01% to about 5% by weight, alternatively from about 0.05% to about 4% by weight, alternatively from about 0.1% to about 3% by weight. Examples of suitable suspension particles are provided in U.S. Pat. No. 7,169,741 and U.S. Patent Publ. No. 2005/0203213, the disclosures of which are incorporated herein by reference. These suspended particles can comprise a liquid core or a solid core. Detailed description of these liquid core and solid core particles, as well as description of preferred particle size, particle shape, particle density, and particle burst strength are described in U.S. patent application Ser. No. 12/370,714, the disclosure of which is incorporated herein by reference.

In one preferred embodiment, the particles may be any discrete and visually distinguishable form of matter, including but not limiting to (deformable) beads, encapsulates, polymeric particles like plastic, metals (e.g. foil material, flakes, glitter), (interference) pigments, minerals (salts, rocks, pebbles, lava, glass/silica particles, talc), plant materials (e.g. pits or seeds, plant fibers, stalks, stems, leaves or roots), solid and liquid crystals, and the like. Different particle shapes are possible, ranging from spherical to tabular.

In one embodiment, the suspension particles may be gas or air bubbles. In this embodiment, the diameter of each bubble may be from about 50 to about 2000 microns and may be present at a level of about 0.01 to about 5% by volume of the composition alternatively from about 0.05% to about 4% by volume of the composition, alternatively from about 0.1% to about 3% by volume of the composition.

Opacifier

In one embodiment, the composition might also comprise an opacifier.

As the term is used herein, an "opacifier" is a substance added to a material in order to make the ensuing system opaque. In one preferred embodiment, the opacifier is Acusol, which is available from Dow Chemicals. Acusol opacifiers are provided in liquid form at a certain % solids level. As supplied, the pH of Acusol opacifiers ranges from 2.0 to 5.0 and particle sizes range from 0.17 to 0.45 um. In one preferred embodiment, Acusol OP303B and 301 can be used.

In yet another embodiment, the opacifier may be an inorganic opacifier. Preferably, the inorganic opacifier can be $TiO_2$, ZnO, talc, $CaCO_3$, and combination thereof. The composite opacifier-microsphere material is readily formed with a preselected specific gravity, so that there is little tendency for the material to separate.

Hydrotrope: The composition may optionally comprises a hydrotrope in an effective amount, i.e. from about 0% to 15%, or about 1% to 10%, or about 3% to about 6%, so that compositions are compatible in water. Suitable hydrotropes for use herein include anionic-type hydrotropes, particularly sodium, potassium, and ammonium xylene sulfonate, sodium, potassium and ammonium toluene sulfonate, sodium potassium and ammonium cumene sulfonate, and mixtures thereof, as disclosed in U.S. Pat. No. 3,915,903.

Anti-oxidant: The composition may optionally contain an anti-oxidant present in the composition from about 0.001 to about 2% by weight. Preferably the antioxidant is present at a concentration in the range 0.01 to 0.08% by weight. Mixtures of anti-oxidants may be used.

Anti-oxidants are substances as described in Kirk-Othmer (Vol. 3, page 424) and In Ullmann's Encyclopedia (Vol. 3, page 91).

One class of anti-oxidants used in the present invention is alkylated phenols, having the general formula:

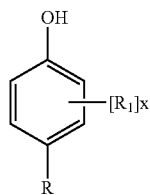

wherein R is $C_1$-$C_{22}$ linear or branched alkyl, preferably methyl or branched $C_3$-$C_6$ alkyl, $C_1$-$C_6$ alkoxy, preferably methoxy; $R_1$ is a $C_3$-$C_6$ branched alkyl, preferably tert-butyl; x is 1 or 2. Hindered phenolic compounds are a preferred type of alkylated phenols having this formula. A preferred hindered phenolic compound of this type is 3,5-di-tert-butyl-4-hydroxytoluene (BHT).

Furthermore, the anti-oxidant used in the composition may be selected from the group consisting of α-, β-, γ-, δ-tocopherol, ethoxyquin, 2,2,4-trimethyl-1,2-dihydroquinoline, 2,6-di-tert-butyl hydroquinone, tert-butyl hydroxyanisole, lignosulphonic acid and salts thereof, and mixtures thereof. It is noted that ethoxyquin (1,2-dihydro-6-ethoxy-2,2,4-trimethylquinoline) is marketed under the name Raluquin™ by the company Raschig™.

Other types of anti-oxidants that may be used in the composition are 6-hydroxy-2,5,7,8-tetramethylchroman-2-carboxylic acid (Trolox™) and 1,2-benzisothiazoline-3-one (Proxel GXL™).

A further class of anti-oxidants which may be suitable for use in the composition is a benzofuran or benzopyran derivative having the formula:

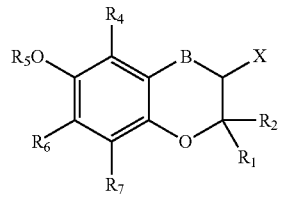

wherein $R_1$ and $R_2$ are each independently alkyl or $R_1$ and $R_2$ can be taken together to form a $C_5$-$C_6$ cyclic hydrocarbyl moiety; B is absent or $CH_2$; $R_4$ is $C_1$-$C_6$ alkyl; $R_5$ is hydrogen or —C(O)$R_3$ wherein $R_3$ is hydrogen or $C_1$-$C_{19}$ alkyl; $R_6$ is $C_1$-$C_6$ alkyl; $R_7$ is hydrogen or $C_1$-$C_6$ alkyl; X is —$CH_2OH$, or —$CH_2A$ wherein A is a nitrogen comprising unit, phenyl, or substituted phenyl. Preferred nitrogen comprising A units include amino, pyrrolidino, piperidino, morpholino, piperazino, and mixtures thereof.

Anti-oxidants such as tocopherol sorbate, butylated hydroxyl benxoic acids and their salts, gallic acid and its alkyl esters, uric acid and its salts, sorbic acid and its salts, and dihydroxyfumaric acid and its salts may also be used. In one aspect, the most preferred types of anti-oxidant for use in the composition are 3,5-di-tert-butyl-4-hydroxytoluene (BHT), α-, β-, γ-, δ-tocopherol, 1,2-benzisothiazoline-3-one (Proxel GXL™) and mixtures thereof.

The cleaning compositions of the present invention may also contain antimicrobial agents. Cationic active ingredients may include but are not limited to n-alkyl dimethyl benzyl ammonium chloride, alkyl dimethyl ethyl benzyl ammonium chloride, dialkyl dimethyl quaternary ammonium compounds such as didecyl dimethyl ammonium chloride, N,N-didecyl-Nmethyl-poly(oxyethyl) ammonium propionate, dioctyl didecyl ammonium chloride, also including quaternary species such as benzethonium chloride and quaternary ammonium compounds with inorganic or organic counter ions such as bromine, carbonate or other moieties including dialkyl dimethyl ammonium carbonates, as well as antimicrobial amines such as Chlorhexidine Gluconate, PHMB (Polyhexamethylene biguanide), salt of a biguanide, a substituted biguanide derivative, an organic salt of a quaternary ammonium containing compound or an inorganic salt of a quaternary ammonium containing compound or mixtures thereof.

Packaging. Any conventional packaging may be used and the packaging may be fully or partially transparent so that the consumer can see the color of the laundry care composition which may be provided or contributed to by the color of the dyes essential to the invention. UV absorbing compounds may be included in some or all of the packaging.

When in the form of a liquid, the laundry care compositions of the invention may be aqueous (typically above 2 wt % or even above 5 or 10 wt % total water, up to 90 or up to 80 wt % or 70 wt % total water) or non-aqueous (typically below 2 wt % total water content). Typically the compositions of the invention will be in the form of an aqueous solution or uniform dispersion or suspension of surfactant, shading dye, and certain optional other ingredients, some of which may normally be in solid form, that have been combined with the normally liquid components of the composition, such as the liquid alcohol ethoxylate nonionic, the aqueous liquid carrier, and any other normally liquid optional ingredients. Such a solution, dispersion or suspension will be acceptably phase stable. When in the form of a liquid, the laundry care compositions of the invention preferably have viscosity from 1 to 1500 centipoises (1-1500 mPa*s), more preferably from 100 to 1000 centipoises (100-1000 mPa*s), and most preferably from 200 to 500 centipoises (200-500 mPa*s) at 20 s-1 and 21° C. Viscosity can be determined by conventional methods. Viscosity may be measured using an AR 550 rheometer from TA instruments using a plate steel spindle at 40 mm diameter and a gap size of 500 μm. The high shear viscosity at 20 s-1 and low shear viscosity at 0.05-1 can be obtained from a logarithmic shear rate sweep from 0.1-1 to 25-1 in 3 minutes time at 21° C. The preferred rheology described therein may be achieved using internal existing structuring with detergent ingredients or by employing an external rheology modifier. More preferably the laundry care compositions, such as detergent liquid compositions have a high shear rate viscosity of from about 100 centipoise to 1500 centipoise, more preferably from 100 to 1000 cps. Unit Dose laundry care compositions, such as detergent liquid compositions have high shear rate viscosity of from 400 to 1000 cps. Laundry care compositions such as laundry softening compositions typically have high shear rate viscosity of from 10 to 1000, more preferably from 10 to 800 cps, most preferably from 10 to 500 cps. Hand dishwashing compositions have high shear rate viscosity of from 300 to 4000 cps, more preferably 300 to 1000 cps.

The liquid compositions, preferably the laundry care composition herein can be prepared by combining the components thereof in any convenient order and by mixing, e.g., agitating, the resulting component combination to form a phase stable liquid laundry care composition. In a process for preparing such compositions, a liquid matrix is formed containing at least a major proportion, or even substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactants and the solid form ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills, are incorporated. As a variation of the composition preparation procedure hereinbefore described, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

The leuco colorants of the present invention have been found to be suitable for use in liquid laundry care compositions having a wide range of pH values. For example, the inventive leuco colorants have been found to be suitable for use in liquid laundry care compositions having a pH of greater than or equal to 10. The inventive leuco colorants have also been found to be suitable for use in liquid laundry care compositions having a pH of less than 10. Thus, the leuco colorant are stable in laundry care compositions having pH values of greater than or equal to 10 and less than or equal to 10.

Pouches. In a preferred embodiment of the invention, the composition is provided in the form of a unitized dose, either tablet form or preferably in the form of a liquid/solid (optionally granules)/gel/paste held within a water-soluble film in what is known as a pouch or pod. The composition can be encapsulated in a single or multi-compartment pouch. Multi-compartment pouches are described in more detail in EP-A-2133410. When the composition is present in a multi-compartment pouch, the composition of the invention may be in one or two or more compartments, thus the dye may be present in one or more compartments, optionally all compartments. Non-shading dyes or pigments or other aesthetics may also be used in one or more compartments. In one embodiment the composition is present in a single compartment of a multi-compartment pouch.

Preferred film materials are polymeric materials. The film material can be obtained, for example, by casting, blow-molding, extrusion or blown extrusion of the polymeric material, as known in the art. Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the level of polymer in the pouch material, for example a PVA polymer, is at least 60%. The polymer can have any weight average molecular weight, preferably from about 1000 to 1,000,000, more preferably from about 10,000 to 300,000 yet more preferably from about 20,000 to 150,000. Mixtures of polymers can also be used as the pouch material. This can be beneficial to control the mechanical and/or dissolution properties of the compartments or pouch, depending on the application thereof and the required needs. Suitable mixtures include for example mixtures wherein one polymer has a higher water-solubility than another polymer, and/or one polymer has a higher mechanical strength than another polymer. Also suitable are mixtures of polymers having different weight average molecular weights, for example a mixture of PVA or a copolymer thereof of a weight average molecular weight of about 10,000-40,000, preferably around 20,000, and of PVA or copolymer thereof, with a weight average molecular weight of about 100,000 to 300,000, preferably around 150,000. Also suitable herein are polymer blend compositions, for example comprising hydrolytically degradable and water-soluble polymer blends such as polylactide and polyvinyl alcohol, obtained by mixing polylactide and polyvinyl alcohol, typically comprising about 1-35% by weight polylactide and about 65% to 99% by weight polyvinyl alcohol. Preferred for use herein are polymers which are from about 60% to about 98% hydrolysed, preferably about 80% to about 90% hydrolysed, to improve the dissolution characteristics of the material.

Naturally, different film material and/or films of different thickness may be employed in making the compartments of the present invention. A benefit in selecting different films is that the resulting compartments may exhibit different solubility or release characteristics.

Most preferred film materials are PVA films known under the MonoSol trade reference M8630, M8900, H8779 and those described in U.S. Pat. Nos. 6,166,117 and 6,787,512 and PVA films of corresponding solubility and deformability characteristics.

The film material herein can also comprise one or more additive ingredients. For example, it can be beneficial to add plasticizers, for example glycerol, ethylene glycol, diethyleneglycol, propylene glycol, sorbitol and mixtures thereof. Other additives include functional detergent additives to be delivered to the wash water, for example organic polymeric dispersants, etc.

Solid Form. As noted previously, the laundry care compositions may be in a solid form. Suitable solid forms include tablets and particulate forms, for example, granular particles, flakes or sheets. Various techniques for forming detergent compositions in such solid forms are well known in the art and may be used herein. In one aspect, for example when the composition is in the form of a granular particle, the leuco colorant is provided in particulate form, optionally including additional but not all components of the laundry detergent composition. The colorant particulate is combined with one or more additional particulates containing a balance of components of the laundry detergent composition. Further, the colorant, optionally including additional but not all components of the laundry care composition, may be provided in an encapsulated form, and the shading dye encapsulate is combined with particulates containing a substantial balance of components of the laundry care composition.

Method of Use. The compositions of this invention, prepared as hereinbefore described, can be used to form aqueous washing/treatment solutions for use in the laundering/treatment of fabrics. Generally, an effective amount of such compositions is added to water, for example in a conventional fabric automatic washing machine, to form such aqueous laundering solutions. The aqueous washing solution so formed is then contacted, typically under agitation, with the fabrics to be laundered/treated therewith. An effective amount of the liquid detergent compositions herein added to water to form aqueous laundering solutions can comprise amounts sufficient to form from about 500 to 7,000 ppm of composition in aqueous washing solution, or from about 1,000 to 3,000 ppm of the laundry care compositions herein will be provided in aqueous washing solution.

Typically, the wash liquor is formed by contacting the laundry care composition with wash water in such an amount so that the concentration of the laundry care composition in the wash liquor is from above 0 g/l to 5 g/l, or from 1 g/l, and to 4.5 g/l, or to 4.0 g/l, or to 3.5 g/l, or to 3.0 g/l, or to 2.5 g/l, or even to 2.0 g/l, or even to 1.5 g/l. The method of laundering fabric or textile may be carried out in a top-loading or front-loading automatic washing machine, or can be used in a hand-wash laundry application. In these applications, the wash liquor formed and concentration of laundry detergent composition in the wash liquor is that of the main wash cycle. Any input of water during any optional rinsing step(s) is not included when determining the volume of the wash liquor.

The wash liquor may comprise 40 liters or less of water, or 30 liters or less, or 20 liters or less, or 10 liters or less, or 8 liters or less, or even 6 liters or less of water. The wash liquor may comprise from above 0 to 15 liters, or from 2 liters, and to 12 liters, or even to 8 liters of water. Typically from 0.01 kg to 2 kg of fabric per liter of wash liquor is dosed into said wash liquor. Typically from 0.01 kg, or from 0.05 kg, or from 0.07 kg, or from 0.10 kg, or from 0.15 kg, or from 0.20 kg, or from 0.25 kg fabric per liter of wash liquor is dosed into said wash liquor. Optionally, 50 g or less, or 45 g or less, or 40 g or less, or 35 g or less, or 30 g or less, or 25 g or less, or 20 g or less, or even 15 g or less, or even 10 g or less of the composition is contacted to water to form the wash liquor. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1. Typically the wash liquor comprising the laundry care composition of the invention has a pH of from 3 to 11.5.

In one aspect, such method comprises the steps of optionally washing and/or rinsing said surface or fabric, contacting said surface or fabric with any composition disclosed in this specification then optionally washing and/or rinsing said surface or fabric is disclosed, with an optional drying step.

Drying of such surfaces or fabrics may be accomplished by any one of the common means employed either in domestic or industrial settings. The fabric may comprise any fabric capable of being laundered in normal consumer or institutional use conditions, and the invention is suitable for cellulosic substrates and in some aspects also suitable for synthetic textiles such as polyester and nylon and for treatment of mixed fabrics and/or fibers comprising synthetic and cellulosic fabrics and/or fibers. As examples of synthetic fabrics are polyester, nylon, these may be present in mixtures with cellulosic fibers, for example, polycotton fabrics. The solution typically has a pH of from 7 to 11, more usually 8 to 10.5. The compositions are typically employed at concentrations from 500 ppm to 5,000 ppm in solution. The water temperatures typically range from about 5° C. to about 90° C. The water to fabric ratio is typically from about 1:1 to about 30:1.

Test Methods

I. Method for Testing Efficiency of a Laundry Care Formulation

Cotton swatches (Testfabrics, Inc. West Pittston, Pa.; Style 464, 100% Cotton, cut to 4"×6") are stripped prior to use by washing at 49° C. two times with AATCC heavy duty liquid laundry detergent nil brightener (1.55 g/L in aqueous solution)

All $L^*$, $a^*$, $b^*$, and Whiteness Index (WI CIE) values for the cotton fabrics are measured on the dry swatches using a LabScan XE reflectance spectrophotometer (HunterLabs, Reston, Va.; D65 illumination, 10° observer, UV light excluded).

A base wash solution is prepared by dissolving the laundry care formulation comprising a leuco colorant (5.23 g/1.0 L) in deionized water. Four stripped cotton swatches are weighed together and placed in a 250 mL Erlenmeyer flask along with four 10 mm glass marbles. A total of three such flasks are prepared.

An aliquot of this wash solution sufficient to provide a 10.0:1.0 liquor:fabric (w/w) ratio is placed into each of the three 250 mL Erlenmeyer flasks. Each flask is dosed with a 1000 gpg stock hardness solution to achieve a final wash hardness of 6 gpg (3:1 Ca:Mg).

The flasks are placed on a Model 75 wrist action shaker (Burrell Scientific, Inc., Pittsburg, Pa.) and agitated at the maximum setting for 12 minutes, after which the wash solution is removed by aspiration, a volume of rinse water (0 gpg) equivalent to the amount of wash solution used is added. Each flask is dosed with a 1000 gpg stock hardness solution to achieve a final rinse hardness of 6 gpg (3:1 Ca:Mg) before agitating 4 more minutes. The rinse is removed by aspiration and the fabric swatches are spun dry (Mini Countertop Spin Dryer, The Laundry Alternative Inc., Nashua, N.H.) for 1 minute, then placed in a food dehydrator set at 135° F. to dry in the dark for 2 hours. Following this drying procedure, the samples can be stored in the dark or exposed to light for varying amounts of time before measuring the properties of the fabric.

Because consumer habits vary greatly throughout the world, the methods used must allow for the possibility of measuring the benefits of leuco compounds across conditions. One such condition is the exposure to light following drying. Some leuco compounds will not exhibit as large a benefit under dark storage as under light storage, so each leuco compound must be tested under both sets of conditions to determine the optimum benefit. Therefore, Method I includes exposure of the dried fabrics to simulated sunlight for various increments of time before measurements are taken, and the LCE value is set to the maximum value obtained from the set of exposure times described below.

A. Dark Conditions Post-Dry

After drying, the fabrics are stored in the dark at room temperature between measurement time points. L*, a*, b*, and Whiteness Index (WI CIE) values for the cotton fabrics are measured at time t=0, 6, 24 and 48 hours after the conclusion of the two hour drying period. The values of the 12 swatches generated for each leuco colorant (three flasks with four swatches each) are averaged to arrive at the sample values for L*, a*, b* and WI CIE at each time point t.

In order to obtain L*, a*, b* and Whiteness Index (WI CIE) values for the control treatment, the above procedure is repeated as described with the following exceptions: (1) the control base wash solution is prepared using AATCC heavy duty liquid laundry detergent nil brightener (5.23 g/1.0 L) in deionized water, and (2) the values of the 12 swatches generated for the control measured after the drying period are averaged to arrive at the sample values for L*, a*, b* and WI CIE and the control value at t=0 is also used as the control values for t=6, 24 and 48 hours.

The leuco colorant efficiency (LCE) of the leuco colorant in the laundry care formulation is calculated based on the data collected at each time point t using the following equation:

$$LCE_t = DE^* = ((L^*_c - L^*_s)^2 + (a^*_c - a^*_s)^2 + (b^*_c - b^*_s)^2)^{1/2}$$

wherein the subscripts c and s respectively refer to the control, i.e., the fabric washed in AATCC heavy duty liquid laundry detergent nil brightener, and the sample, i.e., the fabric washed in the laundry care formulation containing leuco colorant, where the values used to calculate $LCE_t$ are those at the corresponding time points t (0, 6, 24 or 48 hours).

The WI CIE values of the 12 swatches generated for each wash solution (three flasks with four swatches each) are averaged and the change in whiteness index on washing is calculated using the following equation:

$$\Delta WI = WI\ CIE(\text{after wash}) - WI\ CIE(\text{before wash})$$

There will be a separate value for the laundry care formulation ($\Delta WI_{sample}$) and the AATCC HDL nil brightener ($\Delta WI_{control}$). The change in whiteness between the two formulations is given by:

$$\delta\Delta WI = \Delta WI_{sample} - \Delta WI_{control}$$

B. Light Conditions Post-Dry

The specified cotton fabrics post-dry are exposed to simulated sunlight with irradiance of 0.77 W/m² @ 420 nm in an Atlas Xenon Fade-Ometer Ci3000+ (Atlas Material Testing Technology, Mount Prospect, Ill., USA) equipped with Type S Borosilicate inner (Part no. 20277300) and outer (Part no. 20279600) filters, set at 37° C. maximum cabinet temperature, 57° C. maximum black panel temperature (BPT black panel geometry), and 35% RH (relative humidity). Fabrics are exposed for 15 min, 30 min, 45 min, 60 min, 75 min, 90 min, 120 min, and 240 min. The L*, a*, b*, and Whiteness Index (WI CIE) values for the cotton fabrics are measured on the swatches after each exposure period. The calculation of the LCE and the ΔWI value at each exposure time point is as described in Method I.A. above, and the LCE values and the ΔWI values for the sample and control laundry care formulations are set to the maximum values obtained from the set of exposure times listed.

II. Method for Determining Relative Hue Angle (vs. AATCC Control)

The relative hue angle delivered by a leuco colorant to cotton fabrics treated according to Method I described above is determined as follows.

a) The a* and b* values of the 12 swatches from each solution are averaged and the following formulas used to determine Δa* and Δb*:

$$\Delta a^* = a^*_s - a^*_c \text{ and } \Delta b^* = b^*_s - b^*_c$$

wherein the subscripts c and s respectively refer to the fabric washed in AATCC Heavy duty liquid detergent nil brightener (control) and the fabric washed in the laundry care formulation containing leuco colorant (sample).

b) If the absolute value of both Δa* and Δb*<0.25, no Relative Hue Angle (RHA) is calculated. If the absolute value of either Δa* or Δb* is ≥0.25, the RHA is determined using one of the following formulas:

$$RHA = ATAN2(\Delta a^*, \Delta b^*) \text{ for } \Delta b^* \geq 0$$

$$RHA = 360 + ATAN2(\Delta a^*, \Delta b^*) \text{ for } \Delta b^* < 0$$

A relative hue angle can be calculated for each time point where data is collected in either the dark post-dry or light post-dry assessments. Any of these points may be used to satisfy the requirements of a claim.

III. Method for Determining Lightness (L*), Chroma (C*) and Hue (h*) of a Laundry Care Formulation The aesthetic appearance of laundry care formulation is measured on a LabScan XE reflectance spectrophotometer (HunterLabs, Reston, Va.; D65 illumination, 10° observer, UV light excluded) utilizing the Translucent Sample Set (Part no. LSXE-SC-ASSY) including sample cup, ring and disk set, sample cup port insert (1.75″), and opaque cover. Step by step instructions are found in Hunter Labs Applications Note, Vol. 11, No. 3, 2008. The final values for a given laundry care formulation are the average of the values from three external replicate measurements.

The purpose of the ring and disk set is to control the liquid characteristics and extra light interactions (diffusion and transmission) associated with translucent liquid samples, thus making these samples more like the opaque samples the sensor was designed to measure.

When the ring and disk set is used to measure a liquid, the black plastic ring is first placed in the sample cup to fix the internal path length of light through the liquid sample to 10 mm while excluding outside light that can cause measurement interference. The liquid is poured into the cup until the level of liquid is higher than the top of the black ring.

The white ceramic disk is lowered into the liquid until it sits on top of the ring. The disk provides a white background to direct light that has traveled through the liquid back to the detector. A black sample cup cover is then placed over the sample cup to prevent any ambient light from outside the instrument from leaking into the detector. The liquid sample is measured through the bottom of an excellent optical-quality quartz sample cup as part of the ring and disk set, and is used with the accompanying port insert. Step-by-step instructions for using the ring and disk set are provided below.
1. Orient the instrument so that the sample port is facing up. Replace the regular port insert with the special port insert for the sample cup.
2. Standardize the instrument with the special port insert in place.
3. Insert the 10-mm black ring into the cup so that it settles flat on the bottom of the cup.
4. Fill the cup with the liquid sample until the liquid is above the level of the ring.
5. Float the white ceramic disk down through the liquid sample until it rests firmly on top of the black float ring. The goal is to have the sample appear smooth and opaque through the glass bottom of the sample cup.

IV. Method for Determining the Transparency Rating of a Laundry Care Formulation.

A laundry care formulation having an absorbance (measured in a cuvette having a path length of 1.0 cm) greater than 0.301 at every integer wavelength from 400-750 nm is not transparent and is assigned a transparency rating of 0. All other laundry care compositions are transparent and have a transparency rating from 1 to 6.

The Transparency Rating of a transparent laundry care composition may be determined by measuring the absorbance of the composition in the visible light wavelength (400 to 750 nm) in a cuvette having a path length of 1.0 cm. Transparency Rating 1 is defined as having an absorbency in the visible light wavelength (400 to 750 nm) less than or equal to 0.301 at one or more integer wavelengths in the range. This represents a transmittance of about 50%. For purposes of the invention, as long as one integer wavelength in the visible light range has an absorbance less than or equal to 0.301, it is considered to have Transparency Rating 1. Laundry care compositions are considered to have the Transparency Rating indicated in the Table below as long as one integer wavelength in the visible light range has an absorbance less than or equal to the indicated value.

| Transparency Rating | Minimum Abs. (at integer wavelengths from 400-750 nm)≤ |
|---|---|
| 1 | 0.301 |
| 2 | 0.222 |
| 3 | 0.155 |
| 4 | 0.097 |
| 5 | 0.046 |
| 6 | 0.022 |

EXAMPLE 1

Preparation of HDL Laundry Care Compositions.

In about 499.125 gram of AATCC HDL that contains no colorants or optical brightener (1993, distributed by Procter & Gamble, Cincinnati, Ohio), 0.375 g of a Leuco colorant solution (33 wt % Leuco colorant A in PEG 200) and 0.5 g of antioxidant 3,5-bis(1,1-dimethylethyl)-4-hydroxy-benzenepropanoic acid was added. The 500 grams of detergent thus obtained was divided into six samples. One of the six samples was tested as is, i.e., without any additional coloring. The remaining five samples were colored with corresponding commercialized Liquitint™ colorants (Milliken and Company, Spartanburg, S.C.) to obtain detergents that were red, yellow, green, teal blue, and purple.

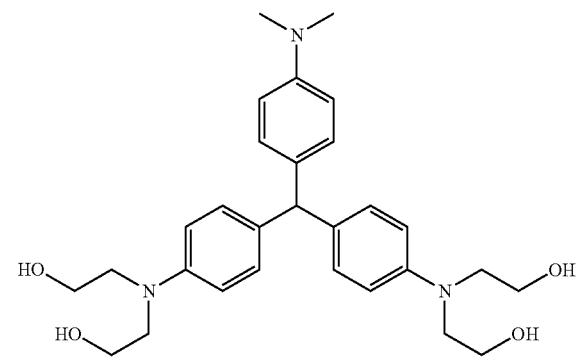

Leuco colorant A

As comparative examples, six additional samples were prepared in the same manner as described above, but without Leuco colorant A or antioxidant. The color of the 12 HDL detergents were read with a Hunter LabScan XE reflectance spectrophotometer using 0.5" glass port, D65 Illuminant, 10° Observer, and UV light excluded. The formulation, appearance, and color reading (L*, a*, b*), as well as the hue angles of all 12 HDL detergents are listed in Table 1.

TABLE 1

Formulation and appearance of colored detergents.

| Example | Leuco colorant A (ppm) | BHT (ppm) | Liquitint ™ Colorant | L* | a* | b* | Hue angle |
|---|---|---|---|---|---|---|---|
| EX1 | 248 | 1000 | None | 31.17 | −3.26 | 6.17 | 118 |
| EX2 | 248 | 1000 | Red ST | 11.95 | 33.49 | 12.11 | 20 |
| EX3 | 248 | 1000 | Bright Yellow | 34.30 | −5.72 | 39.39 | 98 |
| EX4 | 248 | 1000 | Bright Yellow + Blue BUF | 20.47 | −34.32 | 7.06 | 168 |
| EX5 | 248 | 1000 | Blue BUF | 19.86 | −28.49 | −11.09 | 201 |
| EX6 | 248 | 1000 | Blue BUF + Red ST | 1.52 | 4.41 | −7.51 | 300 |

TABLE 1-continued

Formulation and appearance of colored detergents.

| | Leuco colorant A (ppm) | BHT (ppm) | Liquitint ™ Colorant | L* | a* | b* | Hue angle |
|---|---|---|---|---|---|---|---|
| Comparative Examples | | | | | | | |
| CEX1 | 0 | 0 | None | 41.99 | −2.28 | 15.03 | 99 |
| CEX2 | 0 | 0 | Red ST | 18.62 | 40.41 | 22.98 | 30 |
| CEX3 | 0 | 0 | Bright Yellow | 43.27 | −4.14 | 51.38 | 95 |
| CEX4 | 0 | 0 | Bright Yellow + Blue BUF | 28.32 | −41.88 | 12.41 | 163 |
| CEX5 | 0 | 0 | Blue BUF | 24.95 | −32.52 | −10.82 | 198 |
| CEX6 | 0 | 0 | Blue BUF + Red ST | 1.33 | 5.66 | −8.79 | 303 |

It is apparent comparing the hue angles (see Table 2) that incorporation of the leuco colorant does not hinder the ability of formulating the desired finished product color of the liquid detergent, so that many colors of liquid detergent could be prepared containing the leuco colorant.

TABLE 2

Hue angles of the colored detergents from Table 1

| | Colored Detergent | | | | |
|---|---|---|---|---|---|
| | 2 | 3 | 4 | 5 | 6 |
| EX | 20 | 98 | 168 | 201 | 300 |
| CEX | 30 | 95 | 163 | 198 | 303 |

HDL Laundry Care Compositions Used to Wash Cotton Fabrics

The twelve detergents in Table 1 were tested according the method described below.

Unbrightened cotton swatches (Testfabrics, Inc. West Pittston, Pa.; Style 403, 100% Cotton, cut to 2"×4") were stripped prior to use by washing at 49° C. two times with AATCC liquid laundry detergent nil brightener (1 g/L in aqueous solution).

A base wash solution for each detergent in Table 1 above was prepared by dissolving the liquid laundry detergent (5.23 g/1.0 L) in deionized water. Two stripped cotton swatches were weighed together and placed in a 250 mL Erlenmeyer flask along with two 10 mm glass marbles. A total of two such flasks were prepared for each wash solution to be tested.

An aliquot of this wash solution sufficient to provide a 10.0:1.0 liquor:fabric (w/w) ratio was placed into each of the 250 mL Erlenmeyer flasks. Each flask was dosed with a 1000 gpg stock hardness solution to achieve a final wash hardness of 6 gpg (3:1 Ca:Mg).

The flasks were placed on a Model 75 wrist action shaker (Burrell Scientific, Inc., Pittsburg, Pa.) and agitated at the maximum setting for 12 minutes, after which the wash solution was removed by aspiration, a volume of rinse water (0 gpg) equivalent to the amount of wash solution used was added. Each flask was dosed with a 1000 gpg stock hardness solution to achieve a final rinse hardness of 6 gpg (3:1 Ca:Mg) before agitating 4 more minutes. The rinse was removed by aspiration and the fabric swatches were spun dry (Mini Countertop Spin Dryer, The Laundry Alternative Inc., Nashua, N.H.) for 1 minute, then placed in a food dehydrator set at 135° F. to dry in the dark for 2 hours.

24 hours later, L*, a*, and b* values for the cotton fabrics were measured on the dry swatches using a X-Rite Color i7 color spectrophotometer (X-Rite, reflectance mode, D65 illumination, 10° observer, UV excluded). The L*, a*, and b* values of the 4 swatches generated for each of the liquid detergent examples in Table 1 (two flasks with two swatches in each, and each swatch was read twice in the two different spots) were averaged and the leuco colorant efficiency (LCE) of each leuco colorant was calculated using the following equation:

$$LCE = \Delta E^* = ((L^*_c - L^*_s)^2 + (a^*_c - a^*_s)^2 + (b^*_c - b^*_s)^2)^{1/2}$$

wherein the subscripts c and s respectively refer to the control, i.e., the fabric washed in detergent with no leuco colorant (CEX1 in table 1), and the sample, i.e., the fabric washed in detergent containing leuco colorant.

The relative hue angle delivered to cotton fabrics was determined as follows.

a) The a* and b* values of the 4 swatches generated for each of the liquid detergent examples in Table 1 were averaged and the following formulas used to determine Δa* and Δb*:

$$\Delta a^* = a^*_s - a^*_c \text{ and } \Delta b^* = b^*_s - b^*_c$$

wherein the subscripts c and s respectively refer to the fabric washed in detergent with no leuco colorant and the fabric washed in detergent containing leuco colorant.

b) If the absolute value of both Δa* and Δb*<0.3, no Relative Hue Angle (RHA) was calculated. If the absolute value of either Δa* or Δb* is ≥0.3, the RHA was determined using one of the following formulas:

$$RHA = ATAN2(\Delta a^*, \Delta b^*) \text{ for } \Delta b^* \geq 0$$

$$RHA = 360 + ATAN2(\Delta a^*, \Delta b^*) \text{ for } \Delta b^* < 0$$

Results for the twelve detergents in Table 1 tested according this method described above are shown in Table 3, which gathers the L*, a*, b*, $\Delta WI_{CIE}$, ΔE* and Relative Hue Angles (RHA) of the cotton swatches obtained from these wash tests. The calculated ΔHA is also provided.

TABLE 3

Cotton fabric washed with different HDLs in Table 1

| HDL used | L* | a* | b* | $\Delta WI_{CIE}$ | ΔE* | RHA | ΔHA |
|---|---|---|---|---|---|---|---|
| EX1 | 95.81 | −0.35 | 1.27 | 1.78 | 0.94 | 266 | 148 |
| EX2 | 95.84 | −0.29 | 1.22 | 2.09 | 0.96 | 270 | 110 |
| EX3 | 95.86 | −0.36 | 1.24 | 2.00 | 0.94 | 265 | 167 |
| EX4 | 95.86 | −0.36 | 1.30 | 1.78 | 0.89 | 263 | 95 |
| EX5 | 95.79 | −0.31 | 1.14 | 2.31 | 1.05 | 269 | 68 |
| EX6 | 95.76 | −0.27 | 0.98 | 2.93 | 1.20 | 272 | 28 |
| CEX1 | 96.41 | −0.26 | 1.99 | 0.00 | 0.00 | — | — |
| CEX2 | 96.44 | −0.18 | 1.87 | 0.60 | 0.15 | — | — |

TABLE 3-continued

Cotton fabric washed with different HDLs in Table 1

| HDL used | L* | a* | b* | $\Delta WI_{CIE}$ | $\Delta E^*$ | RHA | $\Delta HA$ |
|---|---|---|---|---|---|---|---|
| CEX3 | 96.34 | −0.26 | 1.87 | 0.36 | 0.14 | — | — |
| CEX4 | 96.38 | −0.26 | 1.98 | 0.00 | 0.03 | — | — |
| CEX5 | 96.35 | −0.21 | 1.82 | 0.61 | 0.19 | — | — |
| CEX6 | 96.35 | −0.18 | 1.70 | 1.17 | 0.31 | — | — |

The detergents that do not contain leuco colorants showed essentially no change in Whiteness Index. In contrast, the liquid cleaning compositions of the present invention delivered a consistent whitening effect as evidenced by the change in the CIE Whiteness Index ($\Delta WI_{CIE}$) values, providing shading to the fabric with an average hue angle of about 268° relative to the fabric washed with control HDL (CEX1). This is true regardless of the color of the liquid detergent that was used to wash the fabrics.

EXAMPLE 2

Determination of Bias of Leuco Colorants for Increasing the Whiteness of Aged Garments Over Clean New Garments.

The test was run with a series of leuco colorants A-F (see structures below) according to Method I.A. as found herein for the stripped cotton fabrics with the following exceptions: (a) Style 403 cotton swatches were used (Testfabrics, Inc. West Pittston, Pa.), and (b) the leuco colorants were run using equimolar concentrations of leuco colorant ($2.02 \times 10^{-6}$ M). The test procedure was then rerun as described replacing the stripped cotton with swatches cut from a consumer sourced aged T-shirt fabric (St. Vincent DePaul 4"×6" T-shirt swatches, heavy dingy; purchased from J&R Coordinating Services, Cincinnati, Ohio, USA), where the swatches of the T-shirt had WI CIE values before washing between 39.0 and 46.0. The change in Whiteness Index for both the stripped cotton fabrics and consumer sourced aged T-shirt fabric washed in a composition according to Method I.A. were calculated according to the following equation:

$\Delta WI = WI\ CIE\ \text{after wash} - WI\ CIE\ \text{before wash}.$

The WI CIE values measured at 48 hours after dark drying were used for the above calculation in each instance. The $\Delta WI$ values for the control (AATCC nil-leuco) and sample (AATCC with leuco) were used to calculate the $\delta \Delta AWI$ CIE values according to the equation below:

$\delta \Delta WI\ CIE = \Delta WI_{sample} - \Delta WI_{control}$

Results:

| | | $\delta \Delta WI$ CIE | | |
|---|---|---|---|---|
| Entry | Leuco Colorant[a] | Stripped Cotton[b] | Heavy Dingy[c] | Bias[d] |
| A | 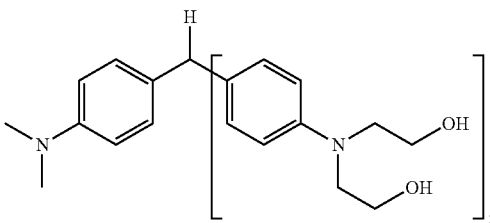 | 1.86 | 17.68 | 9.51 |
| B | 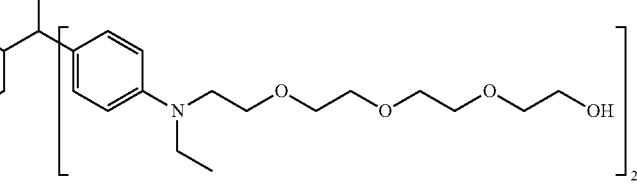 | 1.21 | 14.23 | 11.8 |
| C | 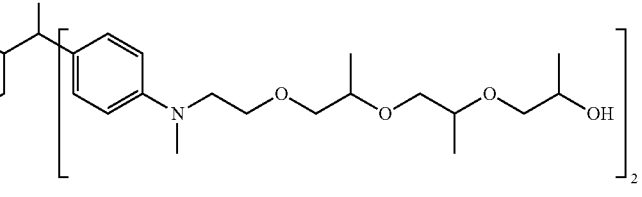 | 0.33 | 16.36 | — |
| D | 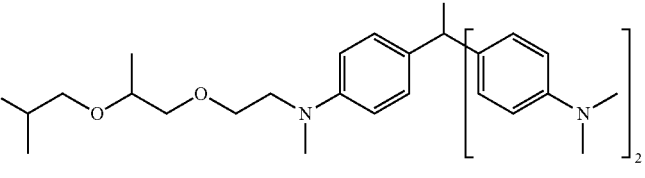 | 0.01 | 18.34 | — |

-continued

| Entry | Leuco Colorant[a] | δΔWI CIE Stripped Cotton[b] | Heavy Dingy[c] | Bias[d] |
|---|---|---|---|---|
| E | (structure: HO-CH₂CH₂-O-CH₂CH₂-N(-CH₂CH₂-O-CH₂CH₂-OH)-C₆H₄-CH(H)-[C₆H₄-N(CH₃)₂]₂) | 0.66 | 14.87 | 22.5 |
| F | (structure: HO-CH₂CH₂-O-CH₂CH₂-O-CH₂CH₂-O-CH₂CH₂-N(-CH₂CH₃)-C₆H₄-CH(H)-[C₆H₄-N(CH₃)₂]₂) | 0.27 | 15.05 | — |

[a]Structure shown is representative.
[b]100% cotton, Style #403, Test Fabrics, Inc., stripped.
[c]100% cotton white T-shirt sourced from consumer (see above for detail).
[d]Value calculated only if δΔWI CIE (48 h) on Stripped Cotton[b] ≥ 0.50.

The data in the table above show that a wide variety of substitutions may be employed in the leuco colorant without losing the ability of the leuco colorant to maintain a strong bias for higher whiteness benefits on aged consumer garments over stripped cotton.

FORMULATION EXAMPLES

The following are illustrative examples of cleaning compositions according to the present disclosure and are not intended to be limiting.

Examples 1-7

Heavy Duty Liquid Laundry Detergent Compositions

| Ingredients | 1 | 2 | 3 | 4 | 5 | 6 | 7 |
|---|---|---|---|---|---|---|---|
|  |  |  |  | % weight |  |  |  |
| $AE_{1.8}S$ | 6.77 | 5.16 | 1.36 | 1.30 | — | — | — |
| $AE_3S$ | — | — | — | — | 0.45 | — | — |
| LAS | 0.86 | 2.06 | 2.72 | 0.68 | 0.95 | 1.56 | 3.55 |
| HSAS | 1.85 | 2.63 | 1.02 | — | — | — | — |
| AE9 | 6.32 | 9.85 | 10.20 | 7.92 | — | — | — |
| AE8 | — | — | — | — | — | — | 35.45 |
| AE7 | — | — | — | — | 8.40 | 12.44 | — |
| $C_{12-14}$ dimethyl Amine Oxide | 0.30 | 0.73 | 0.23 | 0.37 | — | — | — |
| $C_{12-18}$ Fatty Acid | 0.80 | 1.90 | 0.60 | 0.99 | 1.20 | — | 15.00 |
| Citric Acid | 2.50 | 3.96 | 1.88 | 1.98 | 0.90 | 2.50 | 0.60 |
| Optical Brightener 1 | 1.00 | 0.80 | 0.10 | 0.30 | 0.05 | 0.50 | 0.001 |
| Optical Brightener 3 | 0.001 | 0.05 | 0.01 | 0.20 | 0.50 | — | 1.00 |
| Sodium formate | 1.60 | 0.09 | 1.20 | 0.04 | 1.60 | 1.20 | 0.20 |
| DTI | 0.32 | 0.05 | — | 0.60 | — | 0.60 | 0.01 |
| Sodium hydroxide | 2.30 | 3.80 | 1.70 | 1.90 | 1.70 | 2.50 | 2.30 |
| Monoethanolamine | 1.40 | 1.49 | 1.00 | 0.70 | — | — | — |
| Diethylene glycol | 5.50 | — | 4.10 | — | — | — | — |
| Chelant 1 | 0.15 | 0.15 | 0.11 | 0.07 | 0.50 | 0.11 | 0.80 |
| 4-formyl-phenylboronic acid | — | — | — | — | 0.05 | 0.02 | 0.01 |
| Sodium tetraborate | 1.43 | 1.50 | 1.10 | 0.75 | — | 1.07 | — |
| Ethanol | 1.54 | 1.77 | 1.15 | 0.89 | — | 3.00 | 7.00 |
| Polymer 1 | 0.10 | — | — | — | — | — | 2.00 |
| Polymer 2 | 0.30 | 0.33 | 0.23 | 0.17 | — | — | — |
| Polymer 3 | — | — | — | — | — | — | 0.80 |

-continued

| Ingredients | 1 | 2 | 3 | 4 | 5 | 6 | 7 |
|---|---|---|---|---|---|---|---|
| | | | | % weight | | | |
| Polymer 4 | 0.80 | 0.81 | 0.60 | 0.40 | 1.00 | 1.00 | — |
| 1,2-Propanediol | — | 6.60 | — | 3.30 | 0.50 | 2.00 | 8.00 |
| Structurant | 0.10 | — | — | — | — | — | 0.10 |
| Perfume | 1.60 | 1.10 | 1.00 | 0.80 | 0.90 | 1.50 | 1.60 |
| Perfume encapsulate | 0.10 | 0.05 | 0.01 | 0.02 | 0.10 | 0.05 | 0.10 |
| Protease | 0.80 | 0.60 | 0.70 | 0.90 | 0.70 | 0.60 | 1.50 |
| Mannanase | 0.07 | 0.05 | 0.045 | 0.06 | 0.04 | 0.045 | 0.10 |
| Amylase 1 | 0.30 | — | 0.30 | 0.10 | — | 0.40 | 0.10 |
| Amylase 2 | — | 0.20 | 0.10 | 0.15 | 0.07 | — | 0.10 |
| Xyloglucanase | 0.20 | 0.10 | — | — | 0.05 | 0.05 | 0.20 |
| Lipase | 0.40 | 0.20 | 0.30 | 0.10 | 0.20 | — | — |
| Polishing enzyme | — | 0.04 | — | — | — | 0.004 | — |
| Nuclease | 0.05 | — | — | — | — | — | 0.003 |
| Dispersin B | — | — | — | 0.05 | 0.03 | 0.001 | 0.001 |
| Liquitint ® V200 | 0.01 | — | — | — | — | — | 0.005 |
| Leuco colorant | 0.05 | 0.035 | 0.01 | 0.02 | 0.004 | 0.002 | 0.004 |
| Dye control agent | — | 0.3 | — | 0.03 | — | 0.3 | 0.3 |
| Water, dyes & minors | | | | Balance | | | |
| pH | | | | 8.2 | | | |

Based on total cleaning and/or treatment composition weight. Enzyme levels are reported as raw material.

Examples 8 to 18

Unit Dose Compositions

These examples provide various formulations for unit dose laundry detergents. Compositions 8 to 12 comprise a single unit dose compartment. The film used to encapsulate the compositions is polyvinyl-alcohol-based film.

| Ingredients | 8 | 9 | 10 | 11 | 12 |
|---|---|---|---|---|---|
| | | | % weight | | |
| LAS | 19.09 | 16.76 | 8.59 | 6.56 | 3.44 |
| AE3S | 1.91 | 0.74 | 0.18 | 0.46 | 0.07 |
| AE7 | 14.00 | 17.50 | 26.33 | 28.08 | 31.59 |
| Citric Acid | 0.6 | 0.6 | 0.6 | 0.6 | 0.6 |
| C12-15 Fatty Acid | 14.8 | 14.8 | 14.8 | 14.8 | 14.8 |
| Polymer 3 | 4.0 | 4.0 | 4.0 | 4.0 | 4.0 |
| Chelant 2 | 1.2 | 1.2 | 1.2 | 1.2 | 1.2 |
| Optical Brightener 1 | 0.20 | 0.25 | 0.01 | 0.01 | 0.50 |
| Optical Brightener 2 | 0.20 | — | 0.25 | 0.03 | 0.01 |
| Optical Brightener 3 | 0.18 | 0.09 | 0.30 | 0.01 | — |
| DTI | 0.10 | — | 0.20 | — | — |
| Glycerol | 6.1 | 6.1 | 6.1 | 6.1 | 6.1 |
| Monoethanol amine | 8.0 | 8.0 | 8.0 | 8.0 | 8.0 |
| Tri-isopropanol amine | — | — | 2.0 | — | — |
| Tri-ethanol amine | — | 2.0 | — | — | — |
| Cumene sulfonate | — | — | — | — | 2.0 |
| Protease | 0.80 | 0.60 | 0.07 | 1.00 | 1.50 |
| Mannanase | 0.07 | 0.05 | 0.05 | 0.10 | 0.01 |
| Amylase 1 | 0.20 | 0.11 | 0.30 | 0.50 | 0.05 |
| Amylase 2 | 0.11 | 0.20 | 0.10 | — | 0.50 |
| Polishing enzyme | 0.005 | 0.05 | — | — | — |
| Nuclease | 0.— | 0.05 | — | — | 0.005 |
| Dispersin B | 0.010 | 0.05 | 0.005 | 0.005 | — |
| Cyclohexyl dimethanol | — | — | — | 2.0 | — |
| Leuco Colorant | 0.06 | 0.03 | 0.10 | 0.02 | 0.04 |
| Liquitint ® V200 | — | — | 0.01 | 0.05 | — |
| Structurant | 0.14 | 0.14 | 0.14 | 0.14 | 0.14 |
| Perfume | 1.9 | 1.9 | 1.9 | 1.9 | 1.9 |
| Dye control agent | 0.1 | 0.3 | 0.2 | 0.5 | 0.3 |
| Water and miscellaneous | | | To 100% | | |
| pH | | | 7.5-8.2 | | |

Based on total cleaning and/or treatment composition weight. Enzyme levels are reported as raw material.

In the following examples the unit dose has three compartments, but similar compositions can be made with two, four or five compartments. The film used to encapsulate the compartments is polyvinyl alcohol.

| Ingredients | Base compositions | | | |
|---|---|---|---|---|
| | 13 | 14 | 15 | 16 |
| | % weight | | | |
| HLAS | 26.82 | 16.35 | 7.50 | 3.34 |
| AE7 | 17.88 | 16.35 | 22.50 | 30.06 |
| Citric Acid | 0.5 | 0.7 | 0.6 | 0.5 |
| C12-15 Fatty acid | 16.4 | 6.0 | 11.0 | 13.0 |
| Polymer 1 | 2.9 | 0.1 | — | — |
| Polymer 3 | 1.1 | 5.1 | 2.5 | 4.2 |
| Cationic cellulose polymer | — | — | 0.3 | 0.5 |
| Polymer 6 | — | 1.5 | 0.3 | 0.2 |
| Chelant 2 | 1.1 | 2.0 | 0.6 | 1.5 |
| Optical Brightener 1 | 0.20 | 0.25 | 0.01 | 0.005 |
| Optical Brightener 3 | 0.18 | 0.09 | 0.30 | 0.005 |
| DTI | 0.1 | — | 0.05 | — |
| Glycerol | 5.3 | 5.0 | 5.0 | 4.2 |
| Monoethanolamine | 10.0 | 8.1 | 8.4 | 7.6 |
| Polyethylene glycol | — | — | 2.5 | 3.0 |
| Potassium sulfite | 0.2 | 0.3 | 0.5 | 0.7 |
| Protease | 0.80 | 0.60 | 0.40 | 0.80 |
| Amylase 1 | 0.20 | 0.20 | 0.200 | 0.30 |
| Polishing enzyme | — | — | 0.005 | 0.005 |
| Nuclease | 0.05 | — | — | — |
| Dispersin B | — | 0.010 | 0.010 | 0.010 |
| MgCl$_2$ | 0.2 | 0.2 | 0.1 | 0.3 |
| Structurant | 0.2 | 0.1 | 0.2 | 0.2 |
| Acid Violet 50 | 0.04 | 0.03 | 0.05 | 0.03 |
| Perfume/encapsulates | 0.10 | 0.30 | 0.01 | 0.05 |
| Dye control agent | 0.2 | 0.03 | 0.4 | — |
| Solvents and misc. | | To 100% | | |
| pH | | 7.0-8.2 | | |

| | Finishing compositions | | | | | |
|---|---|---|---|---|---|---|
| | 17 | | | 18 | | |
| | Compartment | | | | | |
| | A | B | C | A | B | C |
| | Volume of each compartment | | | | | |
| | 40 ml | 5 ml | 5 ml | 40 ml | 5 ml | 5 ml |
| Ingredients | Active material in Wt. % | | | | | |
| Perfume | 1.6 | 1.6 | 1.6 | 1.6 | 1.6 | 1.6 |
| Liquitint V200 ™ | 0 | 0.006 | 0 | 0 | 0.004 | — |
| Leuco colorant | | 0.02 | | 0.04 | | — |
| TiO2 | — | — | 0.1 | — | | 0.1 |
| Sodium Sulfite | 0.4 | 0.4 | 0.4 | 0.1 | 0.3 | 0.3 |
| Polymer 5 | — | | | 2 | — | — |
| Hydrogenated castor oil | 0.14 | 0.14 | 0.14 | 0.14 | 0.14 | 0.14 |
| Base Composition 13, 14, 15 or 16 | | | | Add to 100% | | |

Based on total cleaning and/or treatment composition weight, enzyme levels are reported as raw material.

| | |
|---|---|
| AE1.8S | is $C_{12-15}$ alkyl ethoxy (1.8) sulfate |
| AE3S | is $C_{12-15}$ alkyl ethoxy (3) sulfate |
| AE7 | is $C_{12-13}$ alcohol ethoxylate, with an average degree of ethoxylation of 7 |
| AE8 | is $C_{12-13}$ alcohol ethoxylate, with an average degree of ethoxylation of 8 |
| AE9 | is $C_{12-13}$ alcohol ethoxylate, with an average degree of ethoxylation of 9 |
| Amylase 1 | is Stainzyme ®, 15 mg active/g, supplied by Novozymes |
| Amylase 2 | is Natalase ®, 29 mg active/g, supplied by Novozymes |
| Xyloglucanase | is Whitezyme ®, 20 mg active/g, supplied by Novozymes |
| Chelant 1 | is diethylene triamine pentaacetic acid |
| Chelant 2 | is 1-hydroxyethane 1,1-diphosphonic acid |
| Dispersin B | is a glycoside hydrolase, reported as 1000 mg active/g |
| DTI | is either poly(4-vinylpyridine-1-oxide) (such as Chromabond S-403E ®), or poly (1-vinylpyrrolidone-co-1-vinylimidazole) (such as Sokalan HP56 ®). |
| Dye control agent | Dye control agent in accordance with the invention, for example Suparex ® O.IN (M1), Nylofixan ® P (M2), Nylofixan ® PM (M3), or Nylofixan ® HF (M4) |
| HSAS | is mid-branched alkyl sulfate as disclosed in U.S. 6,020,303 and U.S. 6,060,443 |
| LAS | is linear alkylbenzenesulfonate having an average aliphatic carbon chain length $C_9$-$C_{15}$ (HLAS is acid form). |
| Leuco colorant | Any suitable leuco colorant or mixtures thereof according to the instant invention. |
| Lipase | is Lipex ®, 18 mg active/g, supplied by Novozymes |
| Liquitint ® V200 | is a thiophene azo dye provided by Milliken |
| Mannanase | is Mannaway ®, 25 mg active/g, supplied by Novozymes |
| Nuclease | is a Phosphodiesterase SEQ ID NO 1, reported as 1000 mg active/g |
| Optical Brightener 1 | is disodium 4,4'-bis {[4-anilino-6-morpholino-s-triazin-2-yl]-amino}-2,2'-stilbenedisulfonate |
| Optical Brightener 2 | is disodium 4,4'-bis-(2-sulfostyryl)biphenyl (sodium salt) |
| Optical Brightener 3 | is Optiblanc SPL10 ® from 3V Sigma |
| Perfume encapsulate | is a core-shell melamine formaldehyde perfume microcapsules. |
| Polishing enzyme | is Para-nitrobenzyl esterase, reported as 1000 mg active/g |
| Polymer 1 | is bis(($C_2H_5O$)($C_2H_4O$)n) ($CH_3$)—$N^+$—$C_xH_{2x}$—$N^+$—($CH_3$)— bis(($C_2H_5O$)($C_2H_4O$)n), wherein n = 20-30, x = 3 to 8 or sulphated or sulfonated variants thereof |
| Polymer 2 | is ethoxylated ($EO_{15}$) tetraethylene pentamine |
| Polymer 3 | is ethoxylated polyethylenimine |
| Polymer 4 | is ethoxylated hexamethylene diamine |
| Polymer 5 | is Acusol 305, provided by Rohm&Haas |
| Polymer 6 | is a polyethylene glycol polymer grafted with vinyl acetate side chains, provided by BASF. |
| Protease | is Purafect Prime ®, 40.6 mg active/g, supplied by DuPont |
| Structurant | is Hydrogenated Castor Oil |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A laundry care composition comprising: (a) at least one laundry care ingredient and (b) a leuco composition, wherein the laundry care composition has a ΔHA of at least 10, wherein the leuco composition is a compound according to formula (I)

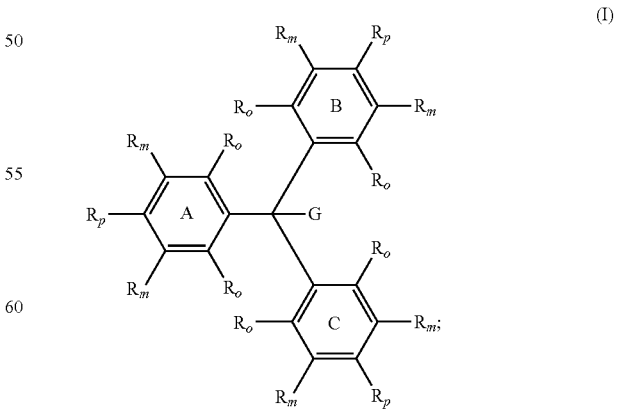

(I)

wherein the ratio of Formula I to its oxidized form is at least 1:3;

wherein all of the $R_o$ and $R_m$ groups on all three rings A, B or C are hydrogen and all three $R_p$ are —$NR^1R^2$;

wherein G is hydrogen;

wherein $R^1$ and $R^2$ are independently selected from the group consisting of hydrogen, alkyl, substituted alkyl, aryl, substituted aryl, alkaryl, substituted alkaryl, and $R^4$; $R^4$ is a organic group composed of one or more organic monomers with said monomer molecular weights ranging from 28 to 500;

wherein any charge present in any of the compounds is balanced with a suitable independently selected internal or external counterion, wherein at least one of $R^1$ and $R^2$ is an $R^4$ that comprises at least two monomers, wherein the leuco composition is uncolored and undergoes color change only when contacted with a triggering agent, wherein the laundry care composition comprises an antioxidant.

2. The laundry care composition of claim 1, wherein the laundry care composition has a ΔHA of at least 25.

3. The laundry care composition of claim 1, wherein the laundry care composition has a ΔHA of at least 90.

4. The laundry care composition of claim 1, wherein $R^4$ is selected from the group consisting of alkyleneoxy, oxoalkyleneoxy, oxoalkyleneamine, epichlorohydrin, quaternized epichlorohydrin, alkyleneamine, hydroxyalkylene, acyloxyalkylene, carboxyalkylene, carboalkoxyalkylene, and sugar.

5. The laundry care composition of claim 1, wherein the laundry care ingredient is selected from the group consisting of surfactants, builders, chelating agents, dye transfer inhibiting agents, dispersants, enzymes, enzyme stabilizers, catalytic materials, bleach activators, polymeric dispersing agents, clay soil removal agents, anti-redeposition agents, brighteners, suds suppressors, dyes, perfume, perfume delivery systems, structurants, fabric softeners, carriers, hydrotropes, processing aids, pigments and mixtures thereof.

6. The laundry care composition of claim 1 having a Transparency Rating of at least 1.

7. A method for treating textile articles comprising the steps of: (a) providing the laundry care composition of claim 1; (b) adding the laundry care composition to a liquid medium; (c) placing textile articles in the liquid medium; (d) optionally, rinsing the textile; and (e) drying the textile articles.

* * * * *